United States Patent
Nagai et al.

(10) Patent No.: US 11,204,552 B2
(45) Date of Patent: Dec. 21, 2021

(54) RADIATION-SENSITIVE COMPOSITION, PATTERN-FORMING METHOD AND RADIATION-SENSITIVE ACID GENERATING AGENT

(71) Applicant: JSR CORPORATION, Tokyo (JP)

(72) Inventors: Tomoki Nagai, Tokyo (JP); Takehiko Naruoka, Tokyo (JP); Ken Maruyama, Tokyo (JP); Motohiro Shiratani, Tokyo (JP); Hisashi Nakagawa, Tokyo (JP)

(73) Assignee: JSR CORPORATION, Tokyo (JP)

( * ) Notice: Subject to any disclaimer, the term of this patent is extended or adjusted under 35 U.S.C. 154(b) by 403 days.

(21) Appl. No.: 15/988,436

(22) Filed: May 24, 2018

(65) Prior Publication Data

US 2018/0267406 A1   Sep. 20, 2018
US 2020/0041902 A9   Feb. 6, 2020

Related U.S. Application Data

(63) Continuation of application No. PCT/JP2016/083609, filed on Nov. 11, 2016.

(30) Foreign Application Priority Data

Dec. 1, 2015 (JP) .............................. JP2015-235237

(51) Int. Cl.
| | |
|---|---|
| G03F 7/004 | (2006.01) |
| G03F 7/039 | (2006.01) |
| G03F 7/30 | (2006.01) |
| G03F 7/38 | (2006.01) |
| C07C 303/32 | (2006.01) |
| C07C 309/06 | (2006.01) |
| C07C 309/12 | (2006.01) |
| C07C 309/19 | (2006.01) |
| C07C 309/24 | (2006.01) |
| C07C 381/12 | (2006.01) |
| G03F 7/20 | (2006.01) |

(52) U.S. Cl.
CPC .......... *G03F 7/0045* (2013.01); *C07C 303/32* (2013.01); *C07C 309/06* (2013.01); *C07C 309/12* (2013.01); *C07C 309/19* (2013.01); *C07C 309/24* (2013.01); *C07C 381/12* (2013.01); *G03F 7/0392* (2013.01); *G03F 7/0397* (2013.01); *G03F 7/30* (2013.01); *G03F 7/38* (2013.01); *G03F 7/2059* (2013.01)

(58) Field of Classification Search
CPC .... G03F 7/0045; G03F 7/0392; G03F 7/0397; G03F 7/2059; G03F 7/30; G03F 7/38; C07C 303/32; C07C 309/06; C07C 309/12; C07C 309/19; C07C 309/24; C07C 381/12

See application file for complete search history.

(56) References Cited

U.S. PATENT DOCUMENTS

| | | | |
|---|---|---|---|
| 6,008,265 A | 12/1999 | Vallee et al. | |
| 6,008,267 A | 12/1999 | Vallee et al. | |
| 6,136,500 A | 10/2000 | Kobayashi et al. | |
| 6,136,501 A | 10/2000 | Trefonas, III et al. | |
| 7,875,417 B2* | 1/2011 | Ogihara | C08L 83/04 430/270.1 |
| 8,283,104 B2* | 10/2012 | Ohashi | G03F 1/50 430/270.1 |
| 2010/0209827 A1* | 8/2010 | Ohashi | C07C 309/12 430/5 |
| 2011/0183264 A1* | 7/2011 | Hashimoto | G03F 7/0045 430/270.1 |
| 2012/0172555 A1* | 7/2012 | Coley | C07C 381/12 526/243 |
| 2012/0172619 A1* | 7/2012 | Coley | C07C 303/32 560/222 |

(Continued)

FOREIGN PATENT DOCUMENTS

| | | |
|---|---|---|
| JP | 8-146610 A | 6/1996 |
| JP | 10-226658 A | 8/1998 |
| JP | 11-125907 A | 5/1999 |

(Continued)

OTHER PUBLICATIONS

Combined Taiwanese Office Action and Search Report dated Jan. 31, 2020 in Taiwanese Patent Application No. 105138327 (with English translation), citing documents AO and AP therein, 21 pages.
International Search Report dated Jan. 31, 2017 in PCT/JP2016/083609 (with English translation), citing documents AO and AP therein. 5 pages.
Written Opinion of the International Searching Authority dated Jan. 31, 2017 in PCT/JP2016/083609 (with English translation), citing documents AO and AP therein,10 pages.
Japanese Office Action dated Sep. 8, 2020 in Japanese Patent Application No. 2017-553743 (with unedited computer generated English translation), 6 pages.

*Primary Examiner* — John S Chu
(74) *Attorney, Agent, or Firm* — Oblon, McClelland, Maier & Neustadt, L.L.P.

(57) ABSTRACT

A radiation-sensitive composition includes: a first polymer having a first structural unit that includes an acid-labile group; and a first compound including a metal cation and a first anion that is a conjugate base of an acid. The acid has a pKa of no greater than 0. The acid is preferably sulfonic acid, nitric acid, organic azinic acid, disulfonylimidic acid or a combination thereof. The first compound is preferably represented by formula (1). In the formula (1), M represents a metal cation; A represents the first anion; x is an integer of 1 to 6; $R^1$ represents a σ ligand; and y is an integer of 0 to 5, and a sum: x+y is no greater than 6. The van der Waals volume of the acid is preferably no less than $2.5 \times 10^{-28}$ m$^3$.

$$[A_xMR^1_y] \qquad (1)$$

17 Claims, 2 Drawing Sheets

(56) References Cited

U.S. PATENT DOCUMENTS

2012/0270155 A1* 10/2012 Komuro ................ C08F 220/28
                                                              430/285.1
2014/0120469 A1* 5/2014 Prokopowicz ........ G03F 7/2041
                                                              430/270.1

FOREIGN PATENT DOCUMENTS

| JP | 2000-298347 A | 10/2000 |
| JP | 2009-134088 A | 6/2009 |
| JP | 2015-172727 A | 10/2015 |
| TW | 200838839 A | 10/2008 |
| TW | 201533538 A | 9/2015 |

* cited by examiner

RADIATION-SENSITIVE COMPOSITION, PATTERN-FORMING METHOD AND RADIATION-SENSITIVE ACID GENERATING AGENT

CROSS-REFERENCE TO RELATED APPLICATIONS

The present application is a continuation application of International Application No. PCT/JP2016/083609, filed Nov. 11, 2016, which claims priority to Japanese Patent Application No. 2015-235237, filed Dec. 1, 2015. The contents of these applications are incorporated herein by reference in their entirety.

BACKGROUND OF THE INVENTION

Field of the Invention

The present invention relates to a radiation-sensitive composition, a pattern-forming method and a radiation-sensitive acid generating agent.

Discussion of the Background

In microfabrication by lithography, a resist film is formed by using a radiation-sensitive composition, and the resist film is irradiated with an electromagnetic wave such as a far ultraviolet ray (ArF excimer laser beam, KrF excimer laser beam, etc.) or an extreme ultraviolet ray (EUV), a charged particle ray such as an electron beam to generate an acid at a light-exposed region. A chemical reaction in which the acid serves as a catalyst causes the difference in rates of dissolution in a developer solution, between light-exposed regions and light-unexposed regions to form a pattern on a substrate.

Such radiation-sensitive compositions are demanded to have improve performances as resist films along with miniaturization in processing techniques. To meet such demands, types, molecular structures and the like of polymers, acid generating agents and other components which may be used in the compositions have been investigated, and combinations thereof have been further investigated in detail (see, Japanese Unexamined Patent Application, Publication Nos. H11-125907, H8-146610 and 2000-298347).

At present, miniaturization of patterns has proceeded to a level for line widths of no greater than 40 nm, and radiation-sensitive compositions are needed to have still superior performances as a resist film, in particular, being highly sensitive even to exposure light such as electron beams and EUV, as well as providing small nanoedge roughness of patterns.

SUMMARY OF THE INVENTION

According to one aspect of the present invention, a radiation-sensitive composition includes: a first polymer having a first structural unit that includes an acid-labile group; and a first compound including a metal cation and a first anion that is a conjugate base of an acid. The acid has a pKa of no greater than 0.

According to another aspect of the present invention, a pattern-forming method includes forming a film from the radiation-sensitive composition. The film is exposed. The exposed film is developed.

According to further aspect of the present invention, a radiation-sensitive acid generating agent includes a compound which include: a metal cation; and an anion that is a conjugate base of an acid. The acid is sulfonic acid, nitric acid, organic azinic acid, disulfonylimidic acid or a combination thereof. The radiation-sensitive acid generating agent is capable of generating the acid by an action of EUV or an electron beam. The acid has a pKa of no greater than 0.

DESCRIPTION OF THE EMBODIMENTS

Figure 1:
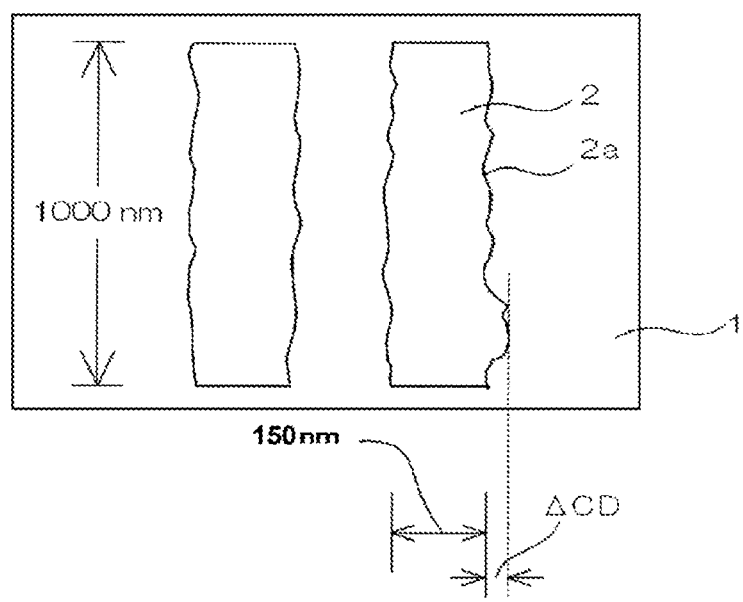
FIG. 1 shows a schematic plan view illustrating a line-pattern when seen from above.

According to an embodiment of the invention made for solving the aforementioned problems, a radiation-sensitive composition contains: a first polymer having a first structural unit that includes an acid-labile group; and a first compound including a metal cation and a first anion that is a conjugate base of an acid (I), the acid (I) having a pKa of no greater than 0.

According to another embodiment of the invention made for solving the aforementioned problems, a pattern-forming method includes: forming a film; exposing the film; and develop the film exposed, wherein the film is formed from the radiation-sensitive composition.

According to still another embodiment of the invention made for solving the aforementioned problems, a radiation-sensitive acid generating agent contains a compound which includes: a metal cation; and an anion that is a conjugate base of an acid being sulfonic acid, nitric acid, organic azinic acid, disulfonylimidic acid or a combination thereof, the radiation-sensitive acid generating agent being capable of generating an acid by an action of EUV or an electron beam, and the acid having a pKa of no greater than 0.

Herein, "metal cation" as referred to means an ion generated from a metal atom through oxidation as a result of electron release. The metal cation may be coordinated with a σ ligand. The "σ ligand" as referred to means a ligand that binds to a metal cation at one or more coordination sites via a σ bond. The term "pKa of an acid" as referred to means a negative logarithm of an acid dissociation constant of the acid, for example, a value at 298 K determined by computation with "Marvin Sketch" plug-in module for computation available from ChemAxon. The "acid-labile group" as referred to means a group being substituted with a hydrogen atom of a carboxy group, a sulfo group, a phenolic hydroxyl group or the like, and a group that is to be dissociated by an action of an acid.

According to the embodiments of the present invention, a radiation-sensitive composition, a pattern-forming method and a radiation-sensitive acid generating agent each enabling superior sensitivity and nanoedge roughness performance to be achieved, are provided.

According to the radiation-sensitive composition and the pattern-forming method of the embodiments of the present invention, formation of a pattern accompanied by small nanoedge roughness is enabled with high sensitivity. The radiation-sensitive acid generating agent of the embodiment of the present invention can be suitably used as an acid generating component of the aforementioned radiation-sensitive composition. Therefore, these can be suitably used in manufacture of semiconductor devices in which further progress of miniaturization is expected in the future.

Radiation-Sensitive Composition

The radiation-sensitive composition of an embodiment of the present invention contains: a first polymer (hereinafter, may be also referred "(A) polymer" or "polymer (A)") having a first structural unit (hereinafter, may be also referred to as "structural unit (I)") that includes an acid-labile group; and a first compound (hereinafter, may be also referred to as "(B) compound" or "compound (B)") including a metal cation (hereinafter, may be also referred to as "cation (I)") and a first anion (hereinafter, may be also referred to as "anion (I)") that is a conjugate base of an acid (hereinafter, may be also referred to as "acid (I)"). The radiation-sensitive composition may contain as a favorable component, a radiation-sensitive acid generator (hereinafter, may be also referred to as "(C) acid generator of acid generator (C)") other than the compound (B), an acid diffusion controller (hereinafter, may be also referred to as "(D) acid diffusion controller" or acid diffusion controller (D)"), a second polymer (hereinafter, may be also referred to as "(E) polymer" or "polymer (E)") having a greater total percentage content by mass of fluorine atoms and silicon atoms greater than the polymer (A), and (F) a solvent, as well as other optional component within a range not leading to impairment of the effects of the present invention. Each component will be described below.

(A) Polymer

The polymer (A) has the structural unit (I). The "polymer" as referred to means a compound formed by linkage of the monomer through generation of a covalent bond, and includes a polymer and an oligomer. The lower limit of the molecular weight of the polymer (A) is, for example, 500, and preferably 1,000. Due to having the structural unit (I), the polymer (A) allows for an action of an acid generated from the compound (B) and/or the acid generator (C) described later, thereby leading to dissociation of the acid-labile group. As a result, solubility of the polymer (A) in a developer solution is altered, whereby the radiation-sensitive composition enables a pattern to be formed.

The polymer (A) is not particularly limited as long as the structural unit (I) is included, and for example, (A1) polymer: a polymer having the structural unit (I), and (A2) polymer: a cyclic oligomer in which a plurality of aromatic rings to which a hydroxy group, which has substituted with the structural unit (I), bonds or a plurality of heteroaromatic rings to which a hydroxy group, which has substituted with the structural unit (I), bonds are linked in a cyclic manner via a hydrocarbon group (calixarene, etc.), and the like.

(A1) Polymer

The polymer (A1) is a polymer having the structural unit (I). In addition to the structural unit (I), the polymer (A1) may have a second structural unit (hereinafter, may be also referred to as "structural unit (II)") represented by the following formula (3) and/or a structural unit (III) that includes a lactone structure, a cyclic carbonate structure, a sultone structure or a combination thereof, as well as other structural unit than the structural units (I) to (III). To the polymer (A1), a variety of structural units may be more conveniently introduced, and thus an adjustment of the solubility in the developer solution is enabled. The radiation-sensitive composition enables various resist performances to be more improved. The polymer (A1) may have one, or two or more types of each structural unit. Each structural unit will be described below.

Structural Unit (I)

The structural unit (I) includes an acid-labile group. Examples of the structural unit (I) in the polymer (A1) include a structural unit represented by the following formula (2-1) (hereinafter, may be also referred to as "structural unit (I-1)"), a structural unit represented by the following formula (2-2) (hereinafter, may be also referred to as "structural unit (I-2)"), and the like.

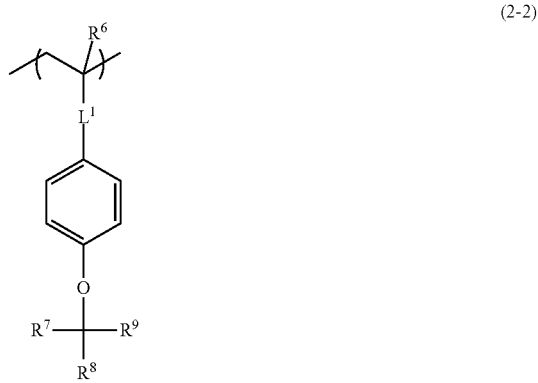

In the above formula (2-1), $R^2$ represents a hydrogen atom, a fluorine atom, a methyl group or a trifluoromethyl group; $R^3$ represents a monovalent hydrocarbon group having 1 to 20 carbon atoms; and $R^4$ and $R^5$ each independently represent a monovalent hydrocarbon group having 1 to 20 carbon atoms, or $R^4$ and $R^5$ taken together represent an alicyclic structure having 3 to ring atoms together with the carbon atom to which $R^4$ and $R^5$ bond.

In the above formula (2-2), $R^6$ represents a hydrogen atom or a methyl group; $L^1$ represents a single bond, —COO— or —CONH—; $R^7$ represents a hydrogen atom or a monovalent hydrocarbon group having 1 to 20 carbon atoms; and $R^8$ and $R^9$ each independently represent a monovalent hydrocarbon group having 1 to 20 carbon atoms, or a monovalent oxyhydrocarbon group having 1 to 20 carbon atoms. The "hydrocarbon group" may include a chain hydrocarbon group, an alicyclic hydrocarbon group and an aromatic hydrocarbon group. The "hydrocarbon group" may be a saturated hydrocarbon group or an unsaturated hydrocarbon group. The "chain hydrocarbon group" as referred to means a hydrocarbon group not including a ring structure but comprising only a chain structure, and both a straight chain hydrocarbon group and a branched hydrocarbon group may be involved. The "alicyclic hydrocarbon group" as referred to means a hydrocarbon group not including an aromatic ring structure but comprising only an alicyclic structure as the ring structure, and both a monocyclic alicyclic hydrocarbon group and a polycyclic alicyclic hydrocarbon group may be involved. However, it is not necessary to be constituted with only the alicyclic structure, and a part thereof may include a chain structure. The "aromatic hydrocarbon group" as referred to means a hydrocarbon group including an aromatic ring structure as the ring structure. However, it is unnecessary to be constituted with only the aromatic ring structure, and a part thereof may include a chain structure and/or an alicyclic structure. The number of "ring atoms" as referred to means the number of atoms constituting the alicyclic structure, the aromatic ring structure, an aliphatic hetero ring structure and an aromatic hetero ring structure, and in the case of the ring being polycyclic, the "ring atoms" means the number of atoms constituting the polycycle.

The structural unit (I-1) is preferably structural units represented by the following formulae (2-1-1) to (2-1-5) (hereinafter, may be also referred to as "structural units (I-1-1) to (I-1-5)"). The structural unit (I-2) is preferably a structural unit represented by the following formula (2-2-1) (hereinafter, may be also referred to as "structural unit (I-2-1)").

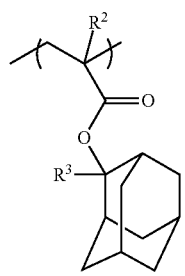
(2-1-1)

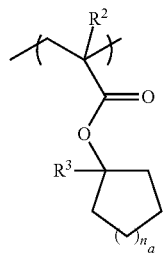
(2-1-2)

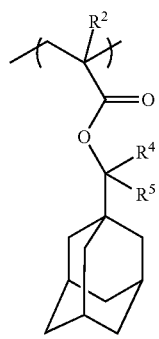
(2-1-3)

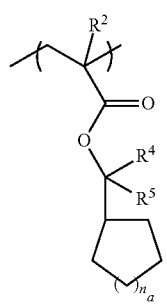
(2-1-4)

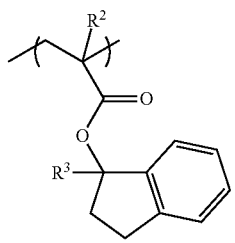
(2-1-5)

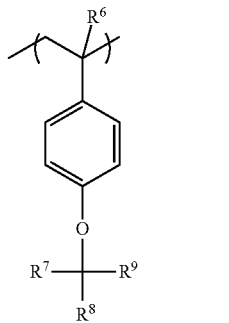
(2-2-1)

In the above formulae (2-1-1) to (2-1-5), $R^2$ to $R^5$ are as defined in the above formula (2-1); and $n_a$ is each independently an integer of 1 to 4.

In the above formula (2-2-1), $R^6$ to $R^9$ are as defined in the above formula (2-2).

Examples of the structural unit (I-1) include structural units represented by the following formulae, and the like.

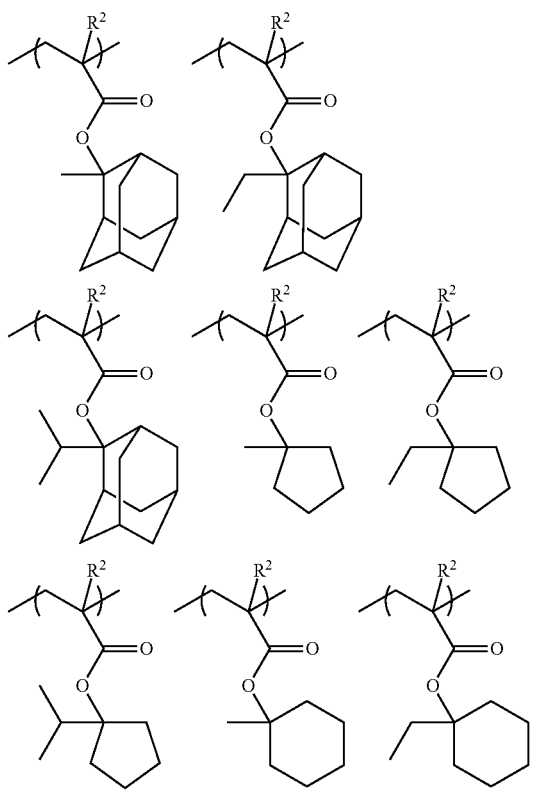

-continued
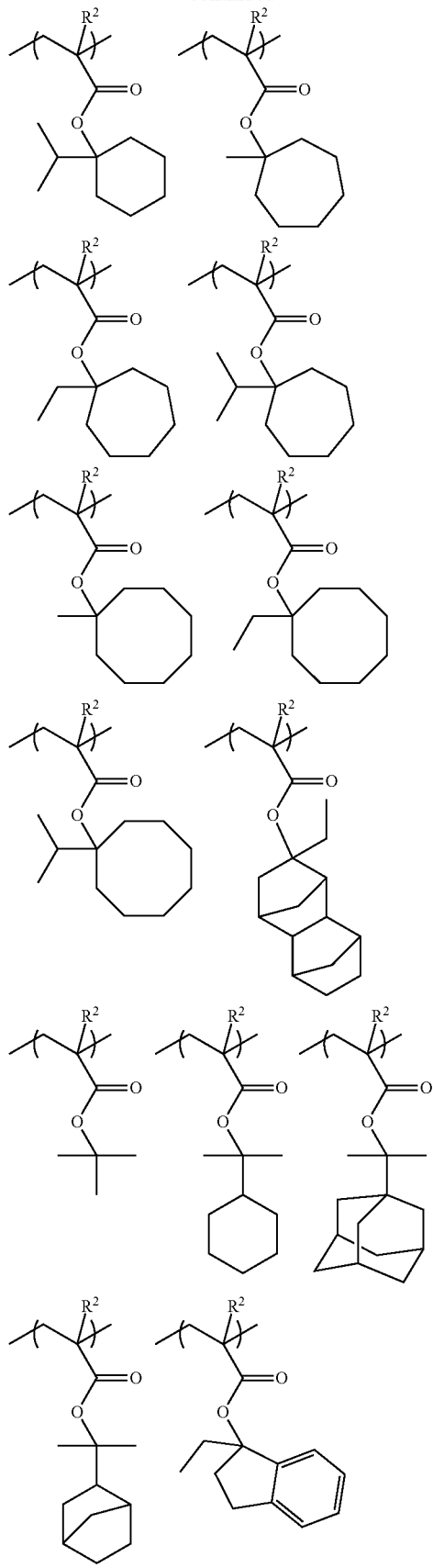
In the above formulae, $R^2$ is as defined in above formula (2-1).
Examples of the structural unit (I-2) include structural units represented by the following formulae, and the like.
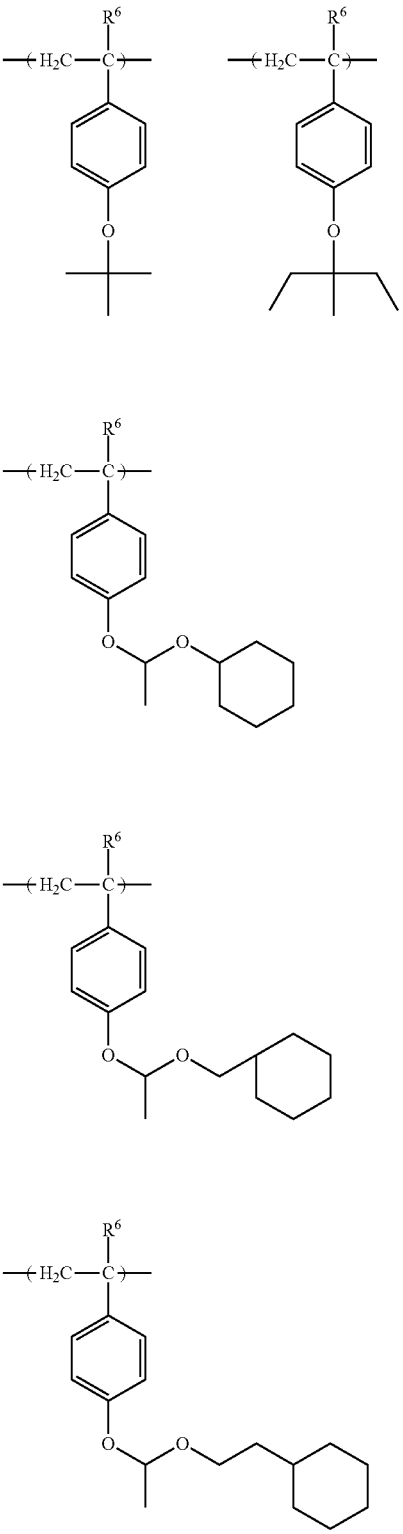

-continued

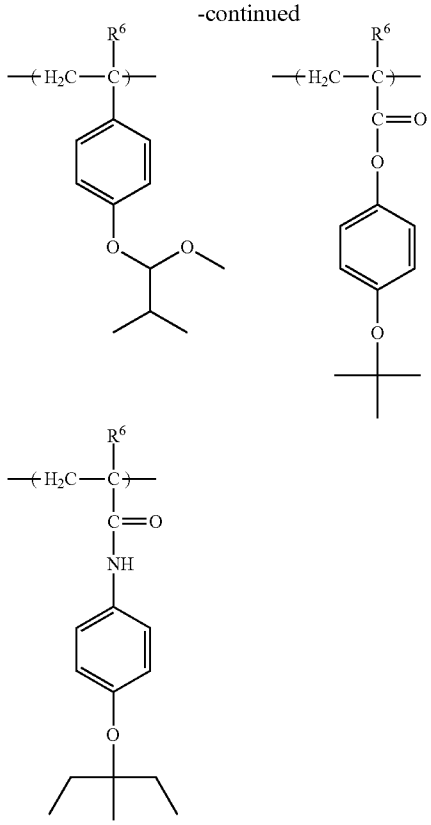

In the above formulae, $R^6$ is as defined in the above formula (2-2).

The structural unit (I-1) is preferably the structural unit (I-1-2), the structural unit (I-1-3) and the structural unit (I-1-5), and more preferably a structural unit derived from 1-alkylcyclopentan-1-yl (meth)acrylate, a structural unit derived from 2-adamantyl-2-propyl (meth)acrylate and a structural unit derived from 1-alkylinden-1-yl (meth)acrylate.

The structural unit (I-2) is preferably the structural unit (I-2-1), more preferably a structural unit derived from p-(1-oxyhydrocarbon-substituted-1-alkyloxy)styrene, still more preferably a structural unit derived from p-(1-cycloalkyloxy-1-alkyloxy)styrene and a structural unit derived from p-(1-alkyloxy-1-alkyloxy)styrene, and particularly preferably a structural unit derived from p-(1-methoxy-2-methyl-propan-1-yloxy)styrene.

The lower limit of the proportion of the structural unit (1) contained with respect to the total structural units constituting the polymer (A1) is preferably mol %, more preferably 20 mol %, still more preferably 30 mol %, and particularly preferably 40 mol %. The upper limit of the proportion is preferably 80 mol %, more preferably 70 mol %, still more preferably 60 mol %, and particularly preferably 55 mol %. When the proportion falls within the above range, further improvements of the sensitivity and the nanoedge roughness performance of the radiation-sensitive composition are enabled.

Structural Unit (II)

The structural unit (II) includes a phenolic hydroxyl group. Due to the structural unit (II), a more appropriate adjustment of the solubility in the developer solution of the polymer (A1) is enabled, and consequently a more improvement of the nanoedge roughness performance of the radiation-sensitive composition is enabled. In addition, a further improvement of adhesiveness of the pattern to the substrate is enabled. Moreover, the sensitivity of the radiation-sensitive composition in the case of employing a KrF exposure, EUV exposure or exposure to an electron beam can be more improved.

Exemplary structural unit (II) includes a structural unit represented by the following formula (3) (hereinafter, may be also referred to as "structural unit (II-1)"), and the like.

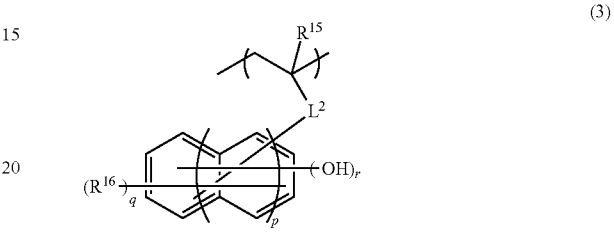

(3)

In the above formula (3), $R^{15}$ represents a hydrogen atom or a methyl group; $L^2$ represents a single bond or a divalent organic group having 1 to 20 carbon atoms; $R^{16}$ represents a monovalent organic group having 1 to 20 carbon atoms; p is an integer of 0 to 2; q is an integer of 0 to 9, wherein in a case where q is no less than 2, a plurality of $R^{16}$s may be identical or different; and r is an integer of 1 to 3.

Examples of the structural unit (II) include structural units represented by the following formulae (3-1) to (3-7) (hereinafter, may be also referred to as "structural units (II-1) to (II-7)"), and the like.

(3-1)

(3-2)

(3-3)

-continued (3-4)
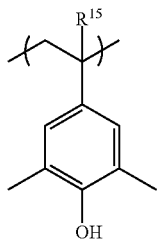

(3-5)
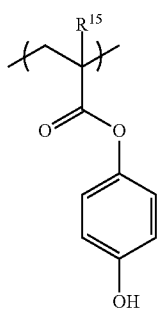

(3-6)
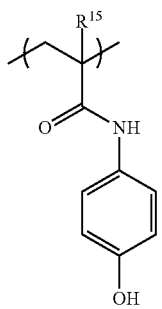

(3-7)
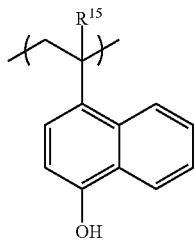

In the above formulae (3-1) to (3-7), $R^{15}$ is as defined in the above formula (3).

Of these, the structural unit (II-1) is preferred.

In a case where the polymer (A1) has the structural unit (II), the lower limit of the proportion of the structural unit (II) contained with respect to the total structural units constituting the polymer (A1) is preferably 10 mol %, more preferably 30 mol %, and more preferably 45 mol %. The upper limit of the proportion is preferably 80 mol %, more preferably 75 mol %, and more preferably 70 mol %. When the proportion of the structural unit (II) falls within the above range, a further improvement of the nanoedge roughness performance of the radiation-sensitive composition is enabled. In addition, the sensitivity in the case of employing a KrF exposure, EUV exposure or exposure to an electron beam can be further improved.

Structural Unit (III)

The structural unit (III) includes a lactone structure, a cyclic carbonate structure, a sultone structure or a combination thereof. Due to the structural unit (III) further having the structural unit (III), a further adjustment of the solubility in the developer solution of the polymer (A1) is enabled, and consequently a more improvement of the nanoedge roughness performance of the radiation-sensitive composition is enabled. In addition, a still further improvement of the adhesiveness of the pattern to the substrate is enabled.

Examples of the structural unit (III) include structural units represented by the following formulae, and the like.

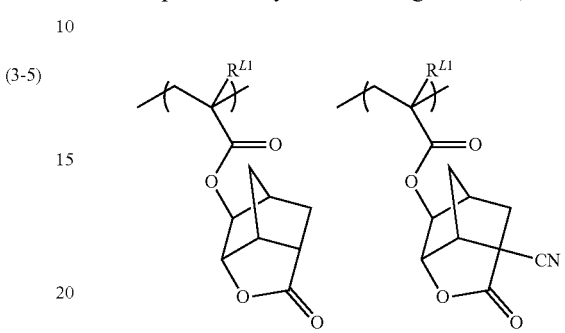

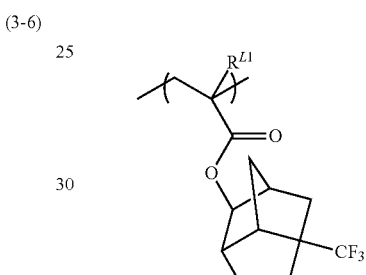

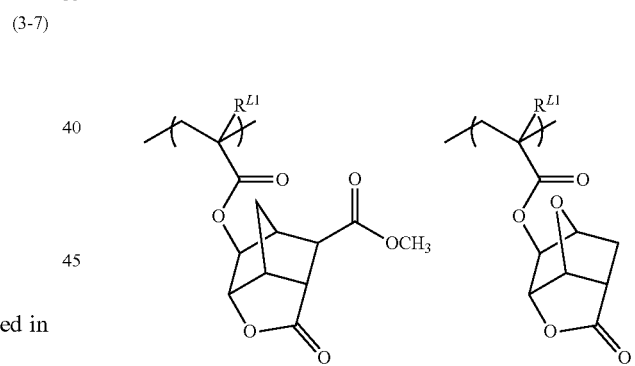

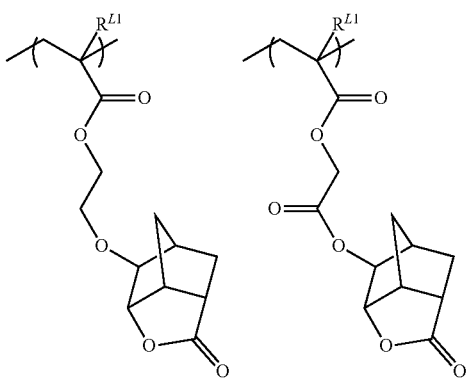

-continued
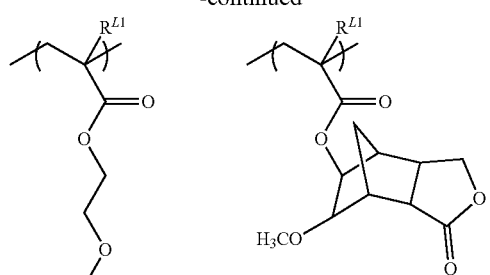
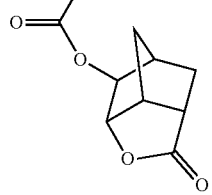
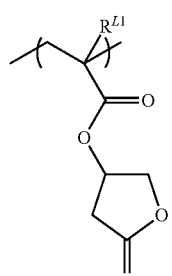 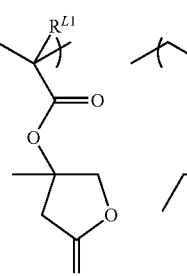
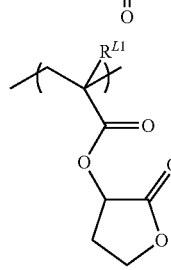 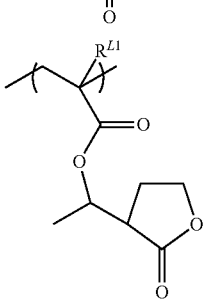
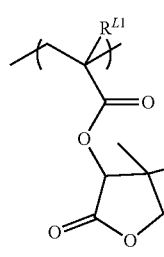 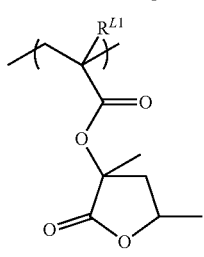
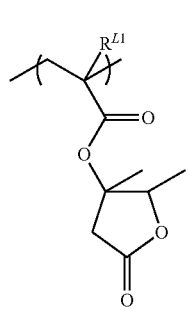 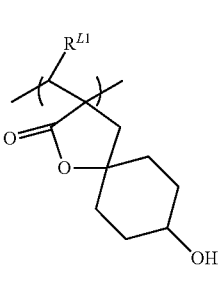
-continued
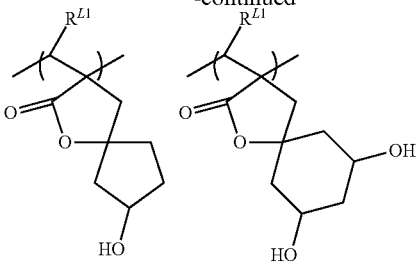
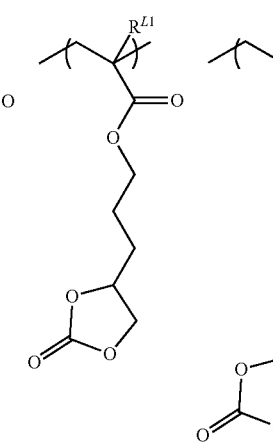

-continued
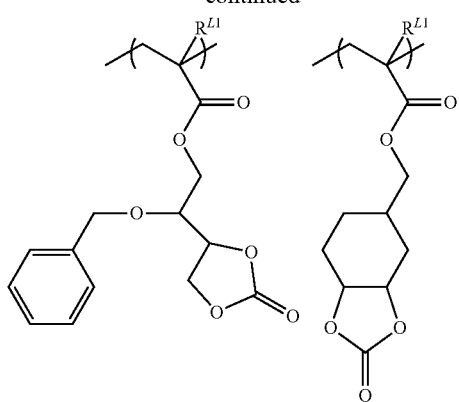
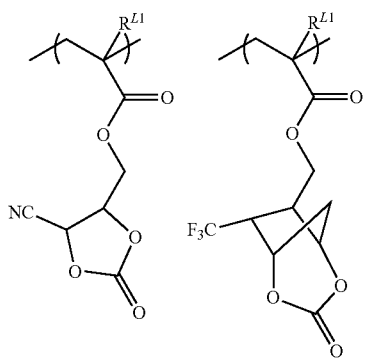
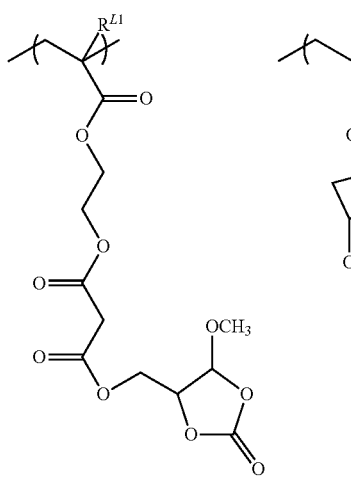
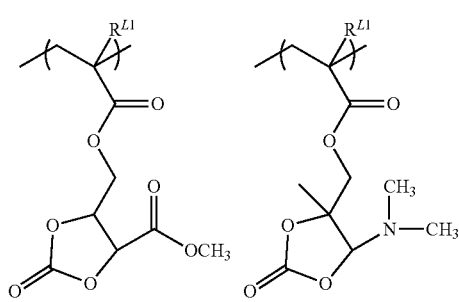
-continued
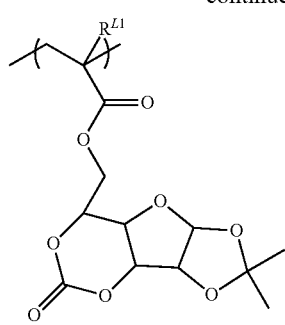
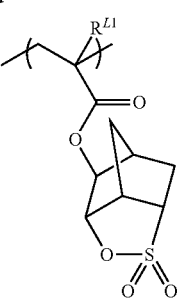
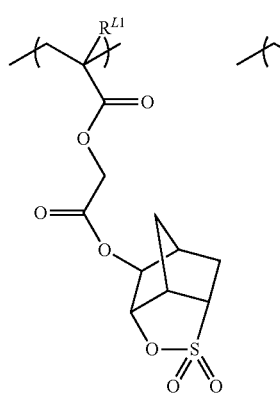
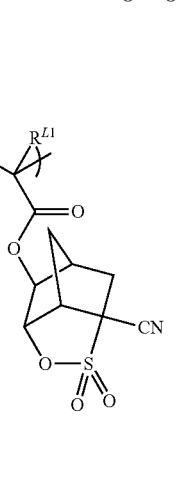
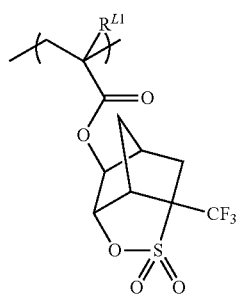
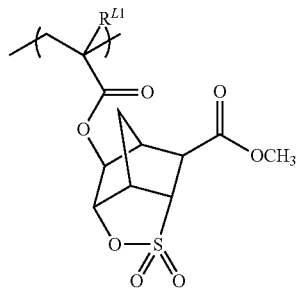
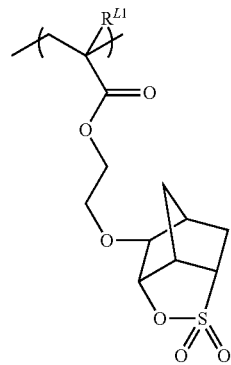

-continued

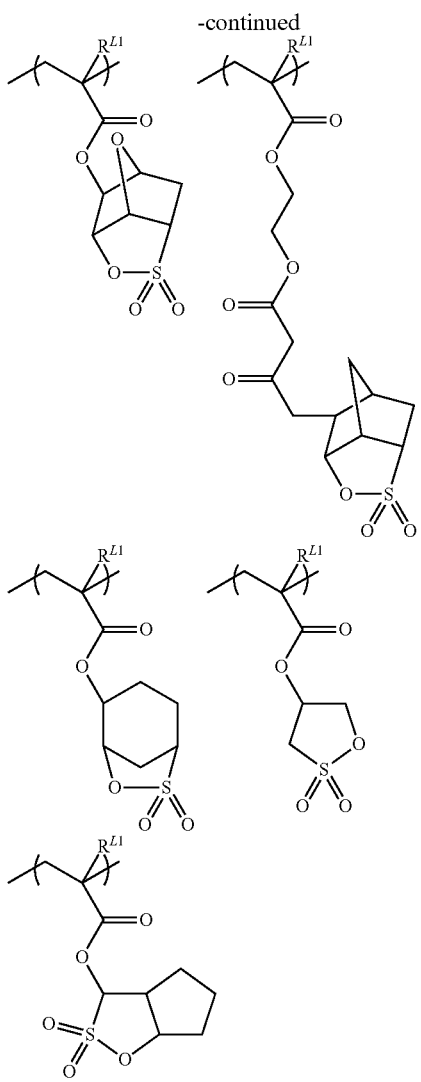

In the above formulae, $R^{L1}$ represents a hydrogen atom, a fluorine atom, a methyl group or a trifluoromethyl group.

Of these, the structural unit (III) is preferably a structural unit that includes a lactone structure, more preferably a structural unit that includes a norbornanelactone structure, and still more preferably a structural unit derived from norbornanelactone-yl (meth)acrylate.

In a case where the polymer (A1) has the structural unit (III), the lower limit of the proportion of the structural unit (III) contained with respect to the total structural units constituting the polymer (A1) is preferably 10 mol %, more preferably 30 mol %, and more preferably 40 mol %. The upper limit of the proportion is preferably 70 mol %, more preferably 60 mol %, and more preferably 50 mol %. When the proportion falls within the above range, a further improvement of the nanoedge roughness performance of the radiation-sensitive composition is enabled. Additionally, a further improvement of the adhesiveness of the pattern to the substrate is enabled.

Other Structural Unit

The polymer (A) may have other structural unit in addition to the structural units (I) to (III). The other structural unit is exemplified by a structural unit that includes a polar group, a structural unit that includes a nonlabile hydrocarbon group, a structural unit derived from aromatic ring-containing cycloalkene, and the like. Examples of the polar group include an alcoholic hydroxyl group, a carboxy group, a cyano group, a nitro group, a sulfonamide group, and the like. Examples of the nonlabile hydrocarbon group include linear alkyl groups, and the like. Examples of the aromatic ring-containing cycloalkene include indene, dihydronaphthalene, acenaphthylene, and the like. The upper limit of the proportion of the other structural unit contained is preferably 20 mol %, more preferably 15 mol %, and more preferably 10 mol %.

The lower limit of polystyrene equivalent weight average molecular weight (Mw) of the polymer (A1) as determined by gel permeation chromatography (GPC) is preferably 1,500, more preferably 2,000, still more preferably 4,000, and particularly preferably 5,000. The upper limit of the Mw is preferably 50,000, more preferably 30,000, still more preferably 20,000, and particularly preferably 10,000. When the Mw of the polymer (A) falls within the above range, further improvements of the sensitivity and the nanoedge roughness performance of the radiation-sensitive composition are enabled.

The upper limit of a ratio (Mw/Mn) of the Mw to polystyrene equivalent number average molecular weight (Mn) of the polymer (A1) as determined by GPC is preferably 5, more preferably 3, and still more preferably 2. The lower limit of the ratio is typically 1, and preferably 1.1.

The Mw and the Mn of the polymer as referred to herein are values determined by using gel permeation chromatography (GPC) under the following conditions.

GPC columns: Tosoh Corporation, "G2000HXL"×2; "G3000HXL"×1; and "G4000HXL"×1 column temperature: 40° C.

elution solvent: tetrahydrofuran (Wako Pure Chemical Industries, Ltd.)

flow rate: 1.0 mL/min sample concentration: 1.0% by mass amount of injected sample: 100 μL detector: differential refractometer standard substance: mono-dispersed polystyrene (A2) Polymer The polymer (A2) is a cyclic oligomer in which a plurality of aromatic rings to which a hydroxy group, which has substituted with the structural unit (I), bonds or a plurality of heteroaromatic rings to which a hydroxy group, which has substituted with the structural unit (I), bonds are linked in a cyclic manner via a hydrocarbon group. Due to containing the polymer (A2), the radiation-sensitive composition enables the nanoedge roughness performance to be more improved. Exemplary structural unit (I) in the polymer (A2) includes a structural unit represented by the following formula (2-3) (hereinafter, may be also referred to as "structural unit (I-3)"), and the like. The polymer (A2) has a structure in which the structural unit (I) is linked via a chain hydrocarbon group.

(2-3)

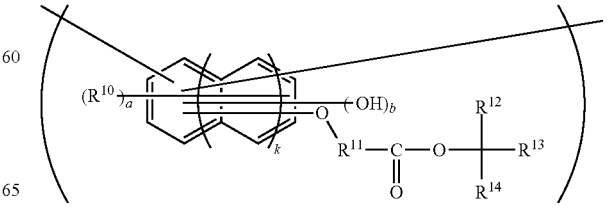

In the above formula (2-3), $R^{10}$ represents a monovalent hydrocarbon group having 1 to 20 carbon atoms or a monovalent oxyhydrocarbon group having 1 to 20 carbon atoms; $R^{11}$ represents a single bond or a divalent hydrocarbon group having 1 to 10 carbon atoms; $R^{12}$ represents a monovalent hydrocarbon group having 1 to 20 carbon atoms; $R^{13}$ and $R^{14}$ each independently represent a monovalent hydrocarbon group having 1 to 20 carbon atoms, or $R^{13}$ and $R^{14}$ taken together represent an alicyclic structure having 3 to ring atoms together with the carbon atom to which $R^{13}$ and $R^{14}$ bond; a is an integer of 0 to 5; b is an integer of 0 to 5, wherein the sum, a+b, is no greater than 5; and k is 0 or 1, wherein in a case where a is no less than 2, a plurality of $R^{10}$s may be identical or different.

The monovalent hydrocarbon group having 1 to 20 carbon atoms and the monovalent oxyhydrocarbon group having 1 to 20 carbon atoms which may be represented by $R^{10}$ are exemplified by a similar group to the monovalent hydrocarbon group exemplified as $R^{P1}$ in the formula (A) of the compound (B) described later, and a group that includes an oxygen atom at the end of the atomic bonding side of the similar group, respectively, and the like.

$R^{10}$ represents preferably an oxyhydrocarbon group, more preferably an alkoxy group, and still more preferably a methoxy group.

The divalent hydrocarbon group having 1 to 10 carbon atoms which may be represented by $R^{11}$ is exemplified by divalent hydrocarbon group each having 1 to 10 carbon atoms among those derived from the groups exemplified as the monovalent hydrocarbon group having 1 to 20 carbon atoms which may be represented by $R^{10}$, by removing one hydrogen atom, and the like.

$R^{11}$ represents preferably a single bond or an alkanediyl group, and more preferably a methanediyl group.

Each group represented by $R^{12}$, $R^{13}$ or $R^{14}$ may be similar to each group exemplified as $R^{3}$, $R^{4}$ or $R^{5}$ in the above formula (2-1), or the like.

In the above formula, "a" is an integer of 0 to 2, and more preferably 1. In the above formula, "b" is an integer of 0 to 2, and more preferably 1.

The polymer (A2) may also have other structural unit in addition to the structural unit (I). The other structural unit is exemplified by a structural unit that includes a phenolic hydroxyl group, and the like.

The lower limit of the molecular weight of the polymer (A2) is preferably 500, more preferably 1,000, and still more preferably 1,500. The upper limit of the molecular weight is preferably 3,000, more preferably 2,000, and still more preferably 1,500. When the molecular weight of the polymer (A2) falls within the above range, further improvements of the sensitivity and the nanoedge roughness performance of the radiation-sensitive composition are enabled.

The lower limit of the content of the polymer (A) with respect to the total solid content of the radiation-sensitive composition is preferably 70% by mass, more preferably 80% by mass, and still more preferably 85% by mass.

Synthesis Method of Polymer (A)

The polymer (A1) may be synthesized, for example, by polymerization of a monomer that gives each structural unit using a radical polymerization initiator, etc., in an appropriate solvent, or by further subjecting a resulting polymer to an appropriate treatment such as acetalization.

Examples of the radical polymerization initiator include: azo-based radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide-based radical initiators such as benzoyl peroxide, t-butyl hydroperoxide and cumene hydroperoxide; and the like. Of these, AIBN and dimethyl 2,2'-azobisisobutyrate are preferred, and AIBN is more preferred. These radical initiator may be used either alone, or as a mixture of two or more types thereof.

Examples of the solvent for use in the polymerization include:

alkanes such as n-pentane, n-hexane, n-heptane, n-octane, n-nonane and n-decane;

cycloalkanes such as cyclohexane, cycloheptane, cyclooctane, decalin and norbornane;

aromatic hydrocarbons such as benzene, toluene, xylene, ethylbenzene and cumene;

halogenated hydrocarbons such as chlorobutanes, bromohexanes, dichloroethanes, hexamethylene dibromide and chlorobenzene;

saturated carboxylic acid esters such as ethyl acetate, n-butyl acetate, i-butyl acetate and methyl propionate;

ketones such as acetone, methyl ethyl ketone, 4-methyl-2-pentanone and 2-heptanone;

ethers such as tetrahydrofuran, dimethoxyethanes and diethoxyethanes;

alcohols such as methanol, ethanol, 1-propanol, 2-propanol and 4-methyl-2-pentanol; and the like. These solvents for use in the polymerization may be used alone, or two or more types thereof may be used in combination.

The lower limit of the reaction temperature in the polymerization is preferably 40° C., and more preferably 50° C. The upper limit of the reaction temperature is preferably 150° C., and more preferably 120° C. The lower limit of the of the reaction time in the polymerization is preferably 1 hr, and more preferably 2 hrs. The upper limit of the reaction time is preferably 48 hrs, and more preferably 24 hrs.

The polymer (A2) may be synthesized by, for example, allowing a compound having a phenolic hydroxyl group represented by the following formula (a) to react with an aldehyde represented by the following formula (b) in the presence of an acid such as trifluoroacetic acid in a solvent such as chloroform, and allowing a resulting compound to react with a compound that provides the acid-labile group such as 2-bromoacetyloxy-2-methyladamantane in the presence of a base such as potassium carbonate in a solvent such as N-methylpyrrolidone.

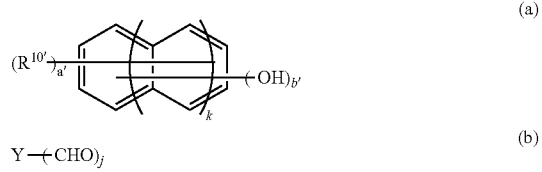

In the above formula (A), $R^{10'}$ represents a hydrocarbon group having 1 to 20 carbon atoms; a' is an integer of 0 to 7; b' is an integer of 1 to 7, wherein, a sum, a'+b' is no greater than 6; and k is 0 or 1, wherein in a case where a' is no less than 2, a plurality of $R^{10'}$s may be identical or different.

In the above formula (b), Y represents a substituted or unsubstituted hydrocarbon group having 1 to 30 carbon atoms and having a valency of j, or a hydrogen atom, and j is 1 or 2.

In the above formula, j is preferably 2; Y represents preferably an unsubstituted divalent hydrocarbon group, more preferably an alkanediyl group, and still more preferably a propanediyl group.

(B) Compound

The compound (B) includes the cation (I) and the anion (I). The compound (B) serves as a radiation-sensitive acid generating agent that is capable of generating the acid (I) by an action of a radioactive ray such as EUV or an electron beam. Due to containing the compound (B) in addition to the polymer (A), the radiation-sensitive composition is superior in the sensitivity and nanoedge roughness performance. Although not necessarily clarified, and without wishing to be bound by any theory, the reason for achieving the effects described above due to the radiation-sensitive composition having the aforementioned constitution may be presumed, for example, as in the following. Specifically, secondary electrons are generated by virtue of the exposure light by an action of the metal cation in the compound (B), and the secondary electron and the anion (I) yield the acid (I). In this instance, the radiation-sensitive composition is considered to attain high sensitivity because of the anion (I) being a conjugate base of the acid (I) having a pKa of no greater than 0, thereby leading to comparatively week coordination ability with the metal, and the like. In addition, it is considered that due to favorable dispersibility of the compound (B) in the film, uniform distribution in the coating film enables the nanoedge roughness of the pattern to be decreased. The cation (I) and the anion (I) will be described below.

Cation (I)

The cation (I) is a metal cation. The cation (I) may be coordinated with the σ ligand. As long as the ligand coordinates to the metal of the cation (I) via a σ-bond, the state of electrons of the metal included in the cation (I) is considered to be maintained, thereby enabling superior sensitivity and nanoedge roughness performance of the radiation-sensitive composition to be maintained. The metal included in the cation (I) is not particularly limited, and may be either a transition metal or a typical metal.

Examples of the cation (I) include cations of elements of group 2, group 3, group 4, group 5, group 6, group 7, group 8, group 9, group 10, group 11 and group 12, and the like. Of these, in light of enhanced sensitivity, cations of elements of group 2, group 3, group 11 and group 12 are preferred.

The cation (1) is preferably a cation of copper, zinc, barium, lanthanum, cerium or silver, in light of further enhanced sensitivity.

Anion (I)

The anion (I) is a conjugate base of the acid (I) having a pKa of no greater than 0.

The upper limit of the pKa of the acid (I) is 0, preferably −1, and more preferably −2. The lower limit of the pKa is preferably −8, more preferably −6, and still more preferably −4. When the pKa of the acid (I) falls within the above range, an improvement of the nanoedge roughness performance of the radiation-sensitive composition is enabled.

Examples of the acid (I) include sulfonic acid, nitric acid, organic azinic acid, disulfonylimidic acid, and the like. The "organic azinic acid" as referred to means a compound represented by $R^XR^YC=N(O)OH$ (wherein, $R^X$ and $R^Y$ each independently represent a monovalent organic group, or $R^X$ and $R^Y$ taken together represent a ring structure together with the carbon atom to which $R^X$ and $R^Y$ bond).

The lower limit of the van der Waals volume of the acid (I) is preferably $1.5 \times 10^{-28}$ m$^3$, more preferably $2.5 \times 10^{-28}$ m$^3$, still more preferably $3.0 \times 10^{-28}$ m$^3$, particularly preferably $3.2 \times 10^{-28}$ m$^3$, and further particularly preferably $3.5 \times 10^{-28}$ m$^3$. Whereas, the upper limit of the van der Waals volume is preferably $1.0 \times 10^{-27}$ m$^3$, and more preferably $6.0 \times 10^{-28}$ m$^3$. When the van der Waals volume falls within the above range, an appropriate decrease in diffusion level of the acid of the radiation-sensitive composition is enabled, leading to a more improvement of the nanoedge roughness performance. The "van der Waals volume" as referred to means a volume of a region occupied by van der Waals spheres based on van der Waals radii of atoms constituting the acid (I), and is a value calculated by determining a stable structure according to a PM3 method by using computation software, for example, WinMOPAC (available from Fujitsu Limited, Ver. 3.9.0) or the like.

Examples of the compound (B) include a compound represented by the following formula (1), and the like.

$$[A_xMR^1_y] \qquad (1)$$

In the above formula (1), M represents a cation (I); A represents anion (I); x is an integer of 1 to 6, wherein in a case where x is no less than 2, a plurality of As may be identical or different; $R^1$ represents a σ ligand; and y is an integer of 0 to 5, wherein in a case where y is no less than 2, a plurality of $R^1$s may be identical or different, and a sum: x+y is no greater than 6.

The cation (I) represented by M is not particularly limited as long as it is a metal cation, and may be a monovalent cation, a divalent cation, a trivalent cation, or a tetravalent cation or a further multivalent cation.

The anion (I) represented by A is not particularly limited as long as it is a conjugate base of the acid (I), and may be a monovalent anion, or a divalent or a further multivalent anion. Of these, a monovalent anion is preferred.

In the above formula, x is preferably 1 to 3.

The σ ligand represented by $R^1$ is exemplified by a monodentate ligand and a polydentate ligand.

Exemplary monodentate ligand includes a hydroxo ligand (OH), a carboxy ligand (COOH), an amide ligand, an acyloxy ligand, an amine ligand, a substituted or unsubstituted hydrocarbon group ligand, and the like.

Examples of the amido ligand include an unsubstituted amido ligand (NH$_2$), a methylamido ligand (NHMe), a dimethylamido ligand (NMe$_2$), a diethylamido ligand (NEt$_2$), a dipropylamido ligand (NPr$_2$), and the like.

Examples of the acyloxy ligand include a formyloxy ligand, an acetyloxy ligand, a propionyloxy ligand, a stearoyloxy ligand, an acryloxy ligand, and the like.

Examples of the amine ligand include a pyridine ligand, a trimethylamine ligand, a piperidine ligand, an ammonia ligand, and the like.

Examples of the hydrocarbon group ligand include: alkyl group ligands such as a methyl group ligand; cycloalkyl group ligands such as a cyclohexyl group ligand; aryl group ligands such as a phenyl group ligand; aralkyl group ligands such as a benzyl group ligand; and the like. A substituent of the hydrocarbon group ligand may be an alkoxy group, a hydroxy group, a halogen atom, or the like.

Exemplary polydentate ligand includes a hydroxyacid ester, a β-diketone, a β-keto ester, a β-dicarboxylic acid ester, an o-acylphenol, a diphosphine, and the like.

Examples of the hydroxyacid ester include glycolic acid esters, lactic acid esters, 2-hydroxycyclohexane-1-carboxylic acid esters, salicylic acid esters, and the like.

Examples of the β-diketone include acetylacetone, 3-methyl-2,4-pentanedione, 3-ethyl-2,4-pentanedione, 2,2-dimethyl-3,5-hexanedione, and the like.

Examples of the β-keto ester include acetoacetic acid esters, α-alkyl-substituted acetoacetic acid esters, β-ketopentanoic acid esters, benzoylacetic acid esters, 1,3-acetonedicarboxylic acid esters, and the like.

Examples of the β-dicarboxylic acid ester include malonic acid diesters, α-alkyl-substituted malonic acid diesters, α-cycloalkyl-substituted malonic acid diesters, α-aryl-substituted malonic acid diesters, and the like.

Examples of the o-acylphenol include o-hydroxyacetophenone, o-hydroxybenzophenone, and the like.

Examples of the diphosphine include 1,1-bis(diphenylphosphino)methane, 1,2-bis(diphenylphosphino)ethane, 1,3-bis(diphenylphosphino)propane, 2,2'-bis(diphenylphosphino)-1,1'-binaphthyl, 1,1'-bis(diphenylphosphino)ferrocene, and the like.

The σ ligand represented by $R^1$ is preferably the acyloxy ligand, the amine ligand, the substituted or unsubstituted hydrocarbon group ligand, the β-diketone and the o-acylphenol, more preferably an acetyloxy ligand, the stearoyloxy ligand, the substituted or unsubstituted aryl group ligand, pyridine, acetylacetone, 3,3-dimethyl-3,5-hexanedione and o-hydroxyacetophenone, and still more preferably a mesityl group ligand.

In the above formula, y is preferably 0 to 3, more preferably 0 to 2, still more preferably 0 and 1, and particularly preferably 0. In other words, the compound (B) is particularly preferably a compound constituted with he cation (I) and the anion (I) (hereinafter, may be also referred to as "acid metal salt").

Examples of the acid metal salt include a sulfonic acid metal salt, a nitric acid metal salt, an organic-azinic acid metal salt, a disulfonylimidic acid metal salt, and the like.

Sulfonic Acid Metal Salt

In a case where the acid (I) is sulfonic acid, the compound (B) is exemplified by a sulfonic acid metal salt represented by the following formula (A) (hereinafter, may be also referred to as "compound (A)"), and the like.

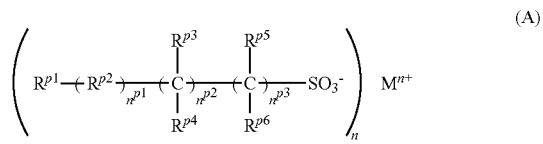

(A)

In the above formula (A), $R^{p1}$ represents a hydrogen atom, a fluorine atom or a monovalent organic group having 1 to 20 carbon atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms, or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; $n^{p3}$ is an integer of 1 to 10, wherein in a case where $n^{p1}$ is no less than 2, a plurality of $R^{p2}$s may be identical or different, in a case where $n^{p2}$ is no less than 2, a plurality of $R^{p3}$s may be identical or different and a plurality of $R^{p4}$s may be identical or different, and in a case where $n^{p3}$ is no less than 2, a plurality of $R^{p5}$s may be identical or different and a plurality of $R^{p6}$s may be identical or different; and $M^{n+}$ represents a cation (I) having a valency of n, wherein n is an integer of 1 to 6.

The monovalent organic group which may be represented by $R^{p1}$ is exemplified by: a monovalent hydrocarbon group having 1 to 20 carbon atoms; a group (a) that includes a divalent hetero atom-containing group between two adjacent carbon atoms of the monovalent hydrocarbon group having 1 to 20 carbon atoms; a group obtained from the monovalent hydrocarbon group having 1 to 20 carbon atoms, or the group (a) by substituting a part or all of hydrogen atoms included therein with a monovalent hetero atom-containing group; and the like.

Exemplary monovalent hydrocarbon group having 1 to 20 carbon atoms includes a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to 20 carbon atoms include:

monocyclic cycloalkyl groups such as a cyclopentyl group and a cyclohexyl group;

monocyclic cycloalkenyl groups such as a cyclopentenyl group and a cyclohexenyl group;

polycyclic cycloalkyl groups such as a norbornyl group, an adamantyl group and a tricyclodecyl group;

polycyclic cycloalkenyl groups such as a norbornenyl group and a tricyclodecenyl group; and the like.

Examples of the monovalent aromatic hydrocarbon group having 6 to 20 carbon atoms include:

aryl groups such as a phenyl group, a tolyl group, a xylyl group, a naphthyl group and an anthryl group;

aralkyl groups such as a benzyl group, a phenethyl group, a naphthylmethyl group and an anthrylmethyl group; and the like.

Examples of the hetero atom constituting the monovalent and divalent hetero atom-containing group include an oxygen atom, a nitrogen atom, a sulfur atom, a phosphorus atom, a silicon atom, a halogen atom, and the like. The halogen atom is exemplified by a fluorine atom, a chlorine atom, a bromine atom, an iodine atom, and the like.

The divalent hetero atom-containing group is exemplified by —O—, —CO—, —S—, —CS—, —NR'—, a group obtained by combining two or more of these, or the like, wherein R' represents a hydrogen atom or a monovalent hydrocarbon group.

Examples of the monovalent hetero atom-containing group include halogen atoms such as a fluorine atom, a chlorine atom, a bromine atom and an iodine atom, a hydroxy group, a carboxy group, a cyano group, an amino group, a sulfanyl group (—SH), and the like.

The monovalent organic group represented by $R^{p1}$ is preferably a monovalent group that includes a ring structure having 6 or more ring atoms. The monovalent group that includes a ring structure having 6 or more ring atoms is exemplified by a monovalent group that includes an alicyclic structure having 6 or more ring atoms, a monovalent group that includes an aliphatic hetero ring structure having 6 or more ring atoms, a monovalent group that includes an aromatic ring structure having 6 or more ring atoms, a monovalent group that includes an aromatic hetero ring structure having 6 or more ring atoms, and the like. When $R^{p1}$ represents the aforementioned group, further appropriate shortening of the diffusion length of the acid (I) is enabled, and as a result, a more improvement of the nanoedge roughness performance of the radiation-sensitive composition is enabled.

Examples of the alicyclic structure having 6 or more ring atoms include:

monocyclic cycloalkane structures such as a cyclohexane structure, a cycloheptane structure, a cyclooctane structure, a cyclononane structure, a cyclodecane structure and a cyclododecane structure;

monocyclic cycloalkene structures such as a cyclohexene structure, a cycloheptene structure, a cyclooctene structure and a cyclodecene structure;

polycyclic cycloalkane structures such as a norbornane structure, an adamantane structure, a tricyclodecane structure and a tetracyclododecane structure;

polycyclic cycloalkene structures such as a norbornene structure and a tricyclodecene structure; and the like.

Examples of the aliphatic hetero ring structure having 6 or more ring atoms include:

lactone structures such as a hexanolactone structure and a norbornanelactone structure;

sultone structures such as a hexanosultone structure and a norbornanesultone structure;

oxygen atom-containing hetero ring structures such as an oxacycloheptane structure and an oxanorbornane structure;

nitrogen atom-containing hetero ring structures such as an azacyclohexane structure and a diazabicyclooctane structure;

sulfur atom-containing hetero ring structures such as a thiacyclohexane structure and a thianorbornane structure; and the like.

Examples of aromatic ring structure having 6 or more ring atoms include a benzene structure, a naphthalene structure, a phenanthrene structure, an anthracene structure, and the like.

Examples of the aromatic hetero ring structure having 6 or more ring atoms include: oxygen atom-containing hetero ring structures such as a pyran structure and a benzopyran structure; nitrogen atom-containing hetero ring structures such as a pyridine structure, a pyrimidine structure and an indole structure; and the like.

The lower limit of the number of the ring atoms of the ring structure in $R^{p1}$ is preferably 7, more preferably 8, still more preferably 9, and particularly preferably 10. Whereas, the upper limit of the number of the ring atoms is preferably 15, more preferably 14, still more preferably 13, and particularly preferably 12. When the number of the ring atoms falls within the above range, further appropriate shortening of the diffusion length of the acid is enabled, and as a result, a more improvement of the nanoedge roughness performance of the radiation-sensitive composition is enabled.

A part or all of hydrogen atoms included in the ring structure in $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, a hydroxy group is preferred.

$R^{p1}$ represents preferably a fluorine atom, a monovalent group that includes an alicyclic structure having 6 or more ring atoms, or a monovalent group that includes an aliphatic hetero ring structure having 6 or more ring atoms, more preferably a fluorine atom, a monovalent group that includes an alicyclic structure having 9 or more ring atoms, or a monovalent group that includes an aliphatic hetero ring structure having 9 or more ring atoms, and still more preferably a fluorine atom, an adamantyl group, a 4-oxo-adamantyl group and a 5,6-(diphenylmethanediyldioxy)norboman-2-yl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. The divalent linking group represented by $R^{p2}$ is preferably a carbonyloxy group, a sulfonyl group, an alkanediyl group and a cycloalkanediyl group, more preferably a carbonyloxy group and a cycloalkanediyl group, still more preferably a carbonyloxy group and a norbornanediyl group, and particularly preferably a carbonyloxy group.

The monovalent hydrocarbon group having 1 to 20 carbon atoms which may be represented by $R^{p3}$ or $R^{p4}$ is exemplified by an alkyl group having 1 to carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each represent preferably a hydrogen atom, a fluorine atom or a fluorinated alkyl group, more preferably a fluorine atom or a perfluoroalkyl group, and still more preferably a fluorine atom or a trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each represent preferably a fluorine atom or a fluorinated alkyl group, more preferably a fluorine atom or a perfluoroalkyl group, still more preferably a fluorine atom or a trifluoromethyl group, and particularly preferably a fluorine atom.

In the above formula, $n^{p1}$ is preferably an integer of 0 to 5, more preferably an integer of 0 to 3, still more preferably an integer of 0 to 2, and particularly preferably 0 and 1.

In the above formula, $n^{p2}$ is preferably an integer of 0 to 5, more preferably an integer of 0 to 2, still more preferably 0 and 1, and particularly preferably 0.

In the above formula, $n^{p3}$ is preferably an integer of 1 to 5, more preferably an integer of 1 to 4, still more preferably an integer of 1 to 3, and particularly preferably 1 and 2.

In the above formula, n is preferably 1 to 5, more preferably 1 to 4, and still more preferably 1 to 3.

Examples of the compound (A) include compounds represented by the following formulae (i-1) to (i-16) (hereinafter, may be referred to as "compounds (i-1) to (i-16)"), and the like.

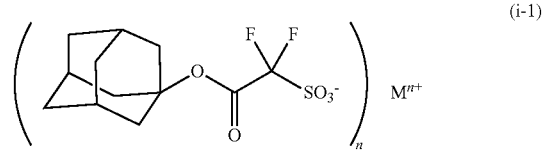

(i-1)

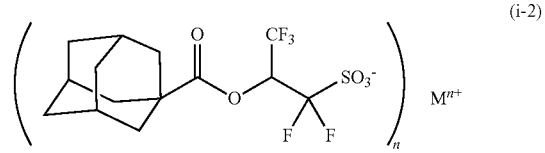

(i-2)

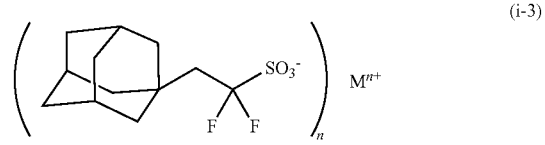

(i-3)

(i-4) 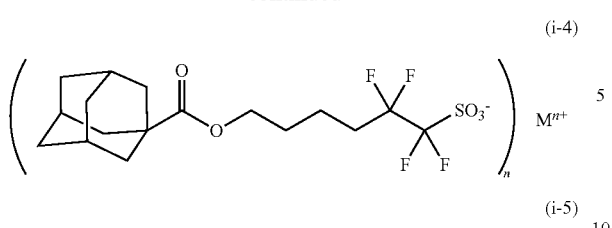

(i-5) 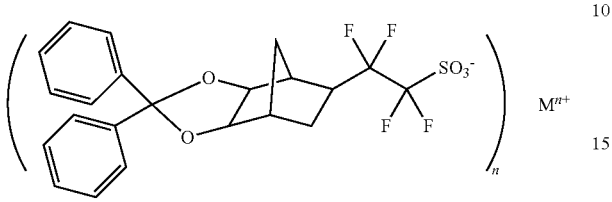

(i-6) 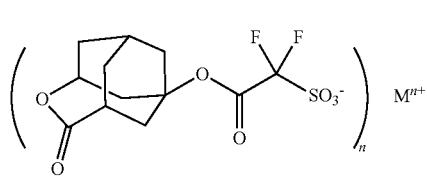

(i-7) 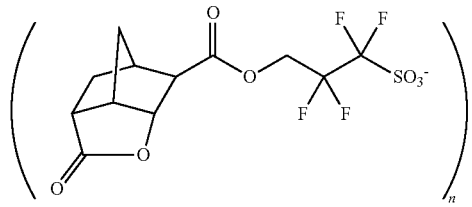

(i-8) 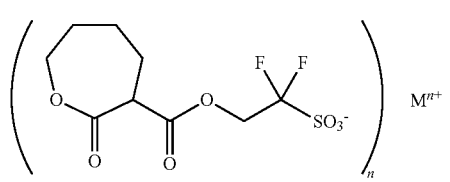

(i-9) 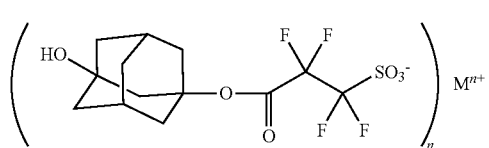

(i-10) 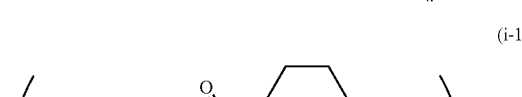

(i-11) 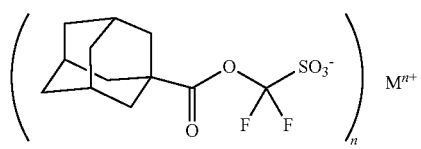

(i-12) 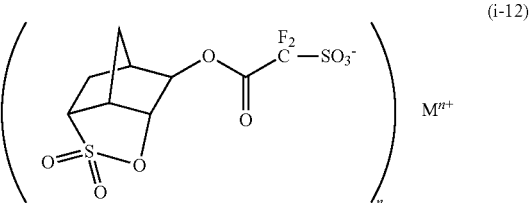

(i-13) 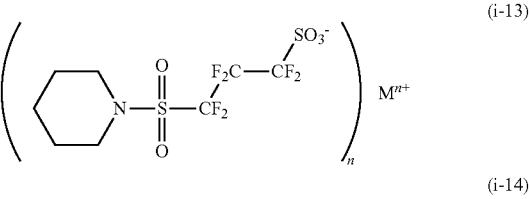

(i-14) 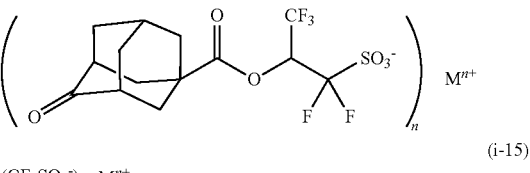

(i-15) $(CF_3SO_3^-)_n$ $M^{n+}$ (i-16) 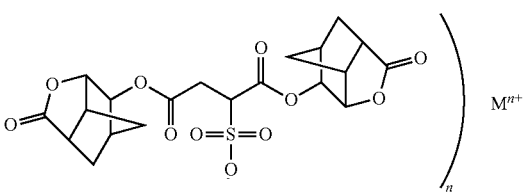

In the above formulae (i-1) to (i-16), $M^{n+}$ represents the cation (I) having a valency of n to which the σ ligand may be coordinated.

The compound (A) is preferably the compound (i-3), the compound (i-5), the compound (i-14), the compound (i-15), the compound (i-16), metal nonafluorobutanesulfonate and metal 2-dodecylbenzenesulfonate, and more preferably a zinc (II) compound represented by the above formula (i-3), a lanthanum (III) compound represented by the above formula (i-5), an indium (III) compound represented by the above formula (i-5), a copper (II) compound represented by the above formula (i-14), a copper (II) compound represented by the above formula (i-15), a zinc (II) compound represented by the above formula (i-15), a cerium (III) compound represented by the above formula (i-15), an yttrium (111) compound represented by the above formula (i-16), barium (II) nonafluorobutanesulfonate and cerium (III) 2-dodecylbenzenesulfonate.

Nitric Acid Metal Salt

In a case where the acid (I) is nitric acid, examples of the compound (B) include nitric acid metal salts such as copper (II) nitrate, zinc (II) nitrate, barium (II) nitrate, lanthanum (III) nitrate, cerium (III) nitrate and silver (1) nitrate, and the like. Of these, lanthanum (III) nitrate is preferred.

Organic-Azinic Acid Metal Salt

In a case where the acid (I) is an organic azinic acid, examples of the compound (B) include organic-azinic acid metal salts such as organic azinate of copper (II), organic azinate of zinc (II), organic azinate of barium (II), organic azinate of lanthanum (III), organic azinate of cerium (III) and organic azinate of silver (I), and the like.

Disulfonylimidic Acid Metal Salt

In a case where the acid (I) is disulfonylimidic acid, exemplary compound (B) includes a disulfonylimidic acid salt represented by the following formula (B) (hereinafter, may be also referred to as "compound (B)"), and the like.

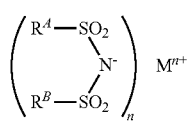
(B)

In the above formula (B), $R^A$ and $R^B$ each independently represent a monovalent organic group having 1 to 20 carbon atoms, or $R^A$ and $R^B$ taken together represent a ring structure having 5 to 20 ring atoms together with the atom chain to which $R^A$ and $R^B$ bond.

Examples of the monovalent organic group having 1 to 20 carbon atoms which may be represented by $R^A$ or $R^B$ include similar groups to those exemplified as the monovalent organic group which may be represented by $R^{p1}$, and the like.

$R^A$ and $R^B$ each represent preferably an alkyl group, a substituted or unsubstituted fluorinated alkyl group, or a substituted or unsubstituted aryl group, more preferably an alkyl group, an organic sulfonyl group-substituted or unsubstituted fluorinated alkyl group, or a fluorine-substituted, chlorine-substituted, nitro-substituted or unsubstituted aryl group, still more preferably an alkyl group, a piperidyl sulfonyl-substituted, cyclohexylphenylsulfonyl-substituted or unsubstituted perfluoroalkyl group, or a fluorine-substituted, trifluoromethyl group-substituted, chlorine-substituted, nitro-substituted or unsubstituted phenyl group, and particularly preferably a methyl group, a piperidylsulfonyl-hexafluoropropyl group, a cyclohexylphenylsulfonyl-hexafluoropropyl group, a trifluoromethyl group, a pentafluoroethyl group, a nonafluorobutyl group, a heptadecafluorooctyl group, a pentafluorophenyl group, a di(trifluoromethyl) phenyl group, a chlorophenyl group, a nitrophenyl group or a phenyl group.

Examples of the ring structure having 3 to 20 ring atoms which may be taken together represented by $R^A$ and $R^B$ groups together with the atom chain to which $R^A$ and $R^B$ bond include sulfonylimide ring structures such as an to ethylenedisulfonylimide ring structure, a propylenedisulfonylimide ring structure, a butylenedisulfonylimide ring structure and a pentylenedisulfonylimide ring structure, and the like.

The group which may be taken together represented by $R^A$ and $R^B$ is preferably a fluorinated alkanediyl group, more preferably a perfluoroalkanediyl group, and still more preferably a tetrafluoroethanediyl group, a hexafluoropropanediyl group and an octafluorobutanediyl group.

Examples of the compound (B) include compounds represented by the following formulas (ii-1) to (ii-26) (hereinafter, may be referred to as "compounds (ii-1) to (ii-26)"), and the like.

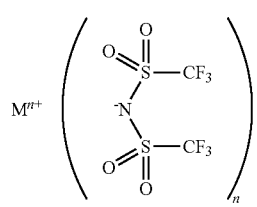
(ii-1)

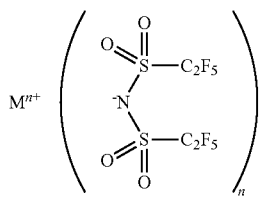
(ii-2)

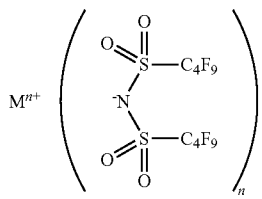
(ii-3)

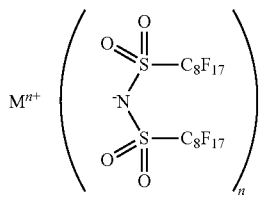
(ii-4)

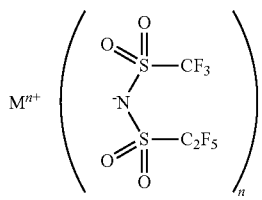
(ii-5)

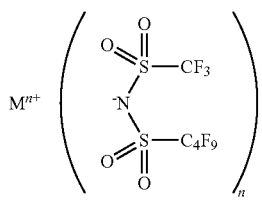
(ii-6)

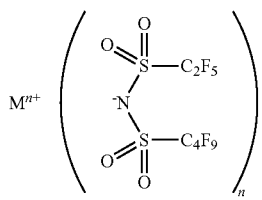
(ii-7)

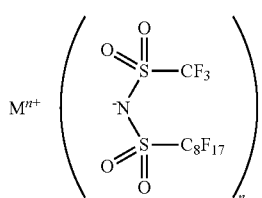
(ii-8)

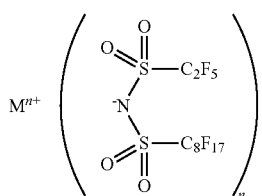
(ii-9)

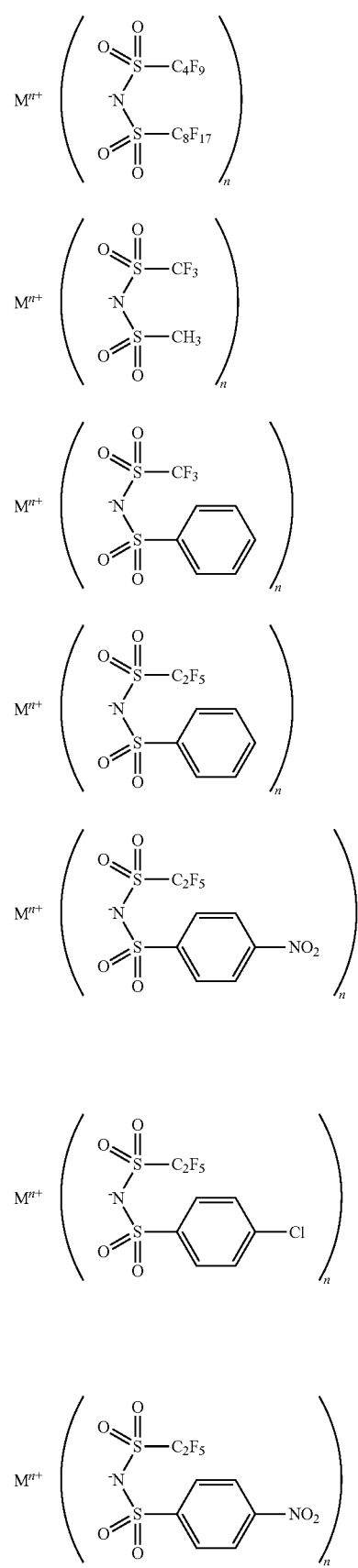
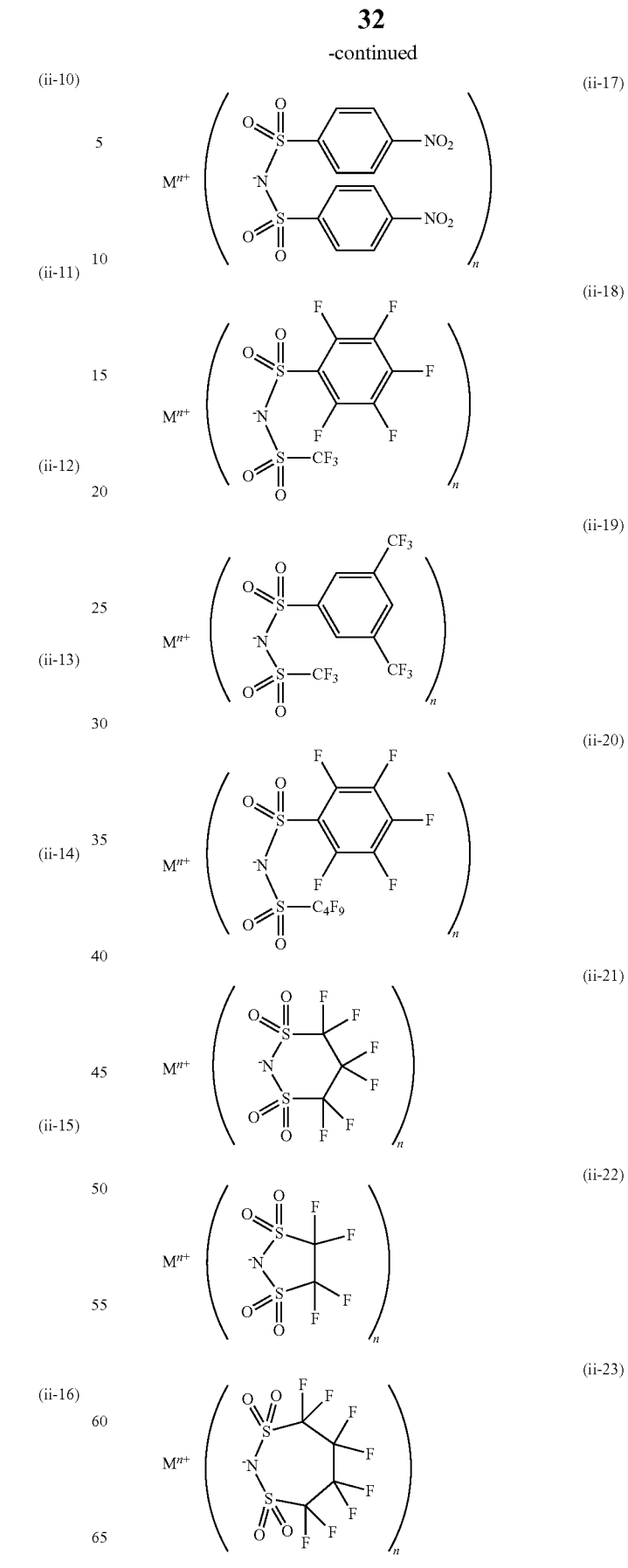

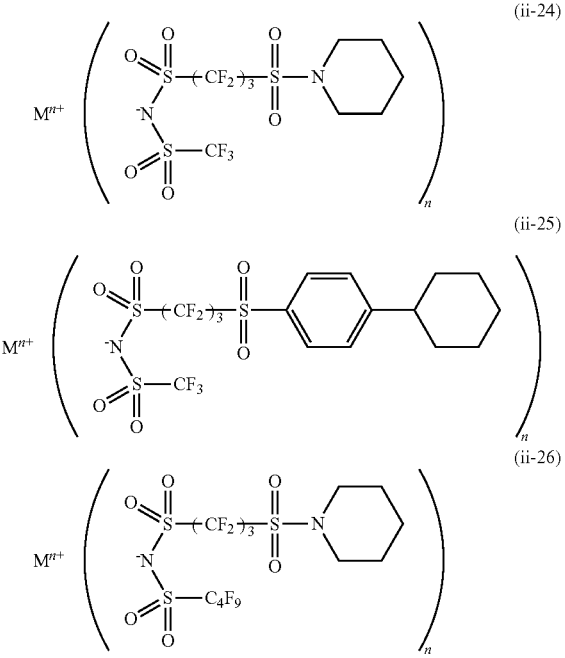

In the above formulae (ii-1) to (ii-26), M$^{n+}$ represents a cation (I) having a valency of n.

The compound (B) is preferably the compound (ii-24), and more preferably a barium (II) compound represented by the above formula (ii-24).

The lower limit of the content of the compound (B) with respect to 100 parts by mass of the polymer (A) is preferably 0.1 parts by mass, more preferably 0.5 parts by mass, more preferably 1 part by mass, particularly preferably 2 parts by mass, and further particularly preferably 2.5 parts by mass. The upper limit of the content is preferably 200 parts by mass, more preferably 100 parts by mass, still more preferably 50 parts by mass, particularly preferably 10 parts by mass, and further particularly preferably 5 parts by mass. When the content of the compound (B) falls within the above range, the radiation-sensitive composition enables a further improvement of the sensitivity and nanoedge roughness performance. The radiation-sensitive composition may contain only one type, or two or more types of the compound (B).

(C) Acid Generator

The acid generator (C) is a radiation-sensitive acid generator other than the compound (B). Since the acid is generated from the compound (B) in the radiation-sensitive composition by an exposure, the acid generator (C) may not be necessarily contained, but due to the radiation-sensitive composition containing the acid generator (C), a further enhancement of the sensitivity of the radiation-sensitive composition is enabled. In the radiation-sensitive composition, the acid generator (C) may be contained either in the form of a low-molecular weight compound as described later (hereinafter, may be also referred to as "(C) acid generating agent" or "acid generating agent (C)" ad libitum) or in the form incorporated as a part of a polymer, or may be in both of these forms.

The acid generating agent (C) is exemplified by an onium salt compound, an N-sulfonyloxyimide compound, a halogen-containing compound, a diazo ketone compound, and the like.

Examples of the onium salt compound include sulfonium salts, tetrahydrothiophenium salts, iodonium salts, phosphonium salts, diazonium salts, pyridinium salts, and the like.

Specific examples of the acid generating agent (C) include the compounds disclosed in paragraphs [0080] to [0113] of Japanese Unexamined Patent Application, Publication No. 2009-134088, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-bicyclo[2.2.1]hept-2-yl-1,1-difluoroethanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 1,1,2,2-tetrafluoro-6-(1-adamantanecarbonyloxy)-hexane-1-sulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-I-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(4-n-butoxynaphthalen-1-yl)tetrahydrothiophenium camphorsulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium camphorsulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy) bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, N-(2-(3-tetracyclo[4.4.0.1$^{2,5}$.1$^{7,10}$]dodecanyl)-1,1-difluoroethanesulfonyloxy)bicyclo[2.2.1]hept-5-ene-2,3-dicarboxyimide, N-(camphorsulfonyloxy)bicyclo[2.2.1]hept-5-ene-2,3-dicarboxyimide, and the like.

As the acid generating agent (C), a compound represented by the following formula (4) may be used. Due to the acid generating agent (C) having the structure described below, an interaction, etc., with a polar structure included in the polymer (A), etc., is considered to result in further appropriate shortening of the diffusion length of the acid generated from the acid generating agent (C) by the exposure in the resist film. As a result, more improvements of various resist performances of the radiation-sensitive composition are enabled.

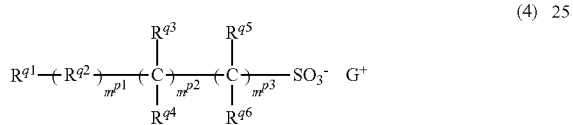

(4)

In the above formula (4), $R^{q1}$ represents a monovalent group that includes a ring structure having 6 or more ring atoms; $R^{q2}$ represents a divalent linking group; $R^{q3}$ and $R^{q4}$ each independently represent a hydrogen atom, a fluorine atom, a monovalent hydrocarbon group having 1 to 20 carbon atoms, or a monovalent fluorinated hydrocarbon group having 1 to 20 carbon atoms; $R^{q5}$ and $R^{q6}$ each independently represent a fluorine atom or a monovalent fluorinated hydrocarbon group having 1 to 20 carbon atoms; $m^{p1}$ is an integer of 0 to 10; $m^{p2}$ is an integer of 0 to 10; $m^{p3}$ is an integer of 1 to 10, wherein in a case where $m^{p1}$ is no less than 2, a plurality of $R^{q2}$s may be identical or different, in a case where $m^{p2}$ is no less than 2, a plurality of $R^{q3}$s may be identical or different and a plurality of $R^{q4}$s may be identical or different, and in a case where $m^{q3}$ is no less than 2, a plurality of $R^{q5}$s may be identical or different and a plurality of $R^{q6}$s may be identical or different; and $G^+$ represents a monovalent radiation-sensitive onium cation.

Each group represented by $R^{q1}$ to $R^{q6}$ may be, for example, each group exemplified as $R^{p1}$ to $R^{p6}$ in the above formula (A), and the like.

The monovalent radiation-sensitive onium cation represented by $G^+$ is degraded by irradiation with exposure light. In light-exposed regions, a sulfonic acid is generated from the sulfonate anion and a proton generated through the degradation of the radiation-sensitive onium cation. The monovalent radiation-sensitive onium cation represented by $G^+$ is exemplified by a radiation-sensitive onium cation containing an element such as S, I, O, N, P, Cl, Br, F, As, Se, Sn, Sb, Te or Bi. Examples of the cation that contains S (sulfur) as the element include a sulfonium cation, a tetrahydrothiophenium cation and the like, whereas examples of the cation that contains I (iodine) as the element include an iodonium cation and the like. Of these, sulfonium cations represented by the following formula (G-1), cations represented by the following formula (G-2), and iodonium cations represented by the following formula (G-3) are preferred.

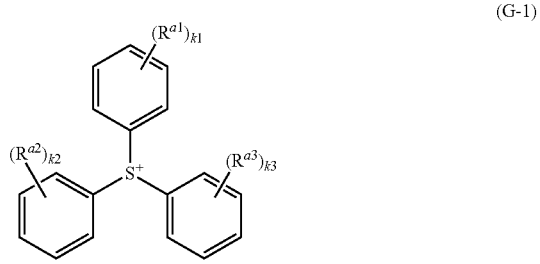

(G-1)

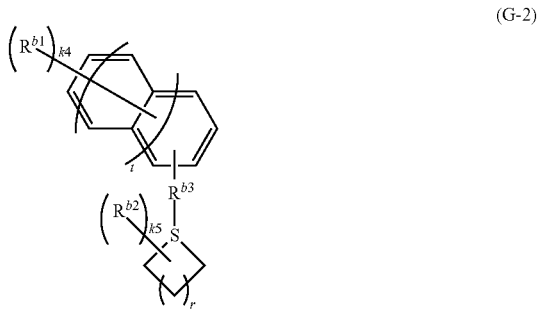

(G-2)

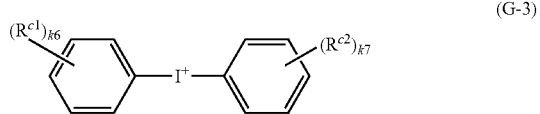

(G-3)

In the above formula (G-1), $R^{a1}$, $R^{a2}$ and $R^{a3}$ each independently represent a substituted or unsubstituted linear or branched alkyl group having 1 to 12 carbon atoms, a substituted or unsubstituted aromatic hydrocarbon group having 6 to 12 carbon atoms, —OSO$_2$—R$^P$ or —SO$_2$—R$^Q$, or at least two of $R^{a1}$, $R^{a2}$ and $R^{a3}$ taken together represent a ring structure; $R^P$ and $R^Q$ each independently represent a substituted or unsubstituted linear or branched alkyl group having 1 to 12 carbon atoms, a substituted or unsubstituted alicyclic hydrocarbon group having 5 to 25 carbon atoms or a substituted or unsubstituted aromatic hydrocarbon group having 6 to 12 carbon atoms; k1, k2 and k3 are each independently an integer of 0 to 5, wherein in a case where $R^{a1}$ to $R^{a3}$, and $R^P$ and $R^Q$ are each present in a plurality of number, a plurality of $R^{a1}$s may be each identical or different, a plurality of $R^{a2}$s may be each identical or different, a plurality of $R^{a3}$s may be each identical or different, a plurality of $R^P$s may be each identical or different, and a plurality of $R^Q$s may be each identical or different.

In the above formula (G-2), $R^{b1}$ represents a substituted or unsubstituted linear or branched alkyl group having 1 to 8 carbon atoms, or a substituted or unsubstituted aromatic hydrocarbon group having 6 to 8 carbon atoms; k4 is an integer of 0 to 7, wherein in a case where $R^{b1}$ is present in a plurality of number, a plurality of $R^{b1}$s may be identical or different, and a plurality of $R^{b1}$s may taken together represent a ring structure; $R^{b2}$ represents a substituted or unsubstituted linear or branched alkyl group having 1 to 7 carbon atoms, or a substituted or unsubstituted aromatic hydrocarbon group having 6 or 7 carbon atoms; k5 is an integer of 0 to 6, wherein in a case where $R^{b2}$ is present in a plurality of number, a plurality of $R^{b2}$s may be identical or different, and a plurality of $R^{b2}$s may taken together represent a ring structure; and r is an integer of 0 to 3; $R^{b3}$ represents a single bond or a divalent organic group having 1 to 20 carbon atoms; and t is an integer of 0 to 2.

In the above formula (G-3), $R^{c1}$ and $R^{c2}$ each independently represent a substituted or unsubstituted linear or branched alkyl group having 1 to 12 carbon atoms, a substituted or unsubstituted aromatic hydrocarbon group having 6 to 12 carbon atoms, $-OSO_2-R^R$ or $-SO_2-R^S$, or at least two of these groups taken together represent a ring structure; $R^R$ and $R^S$ each independently represent a substituted or unsubstituted linear or branched alkyl group having 1 to 12 carbon atoms, a substituted or unsubstituted alicyclic hydrocarbon group having 5 to 25 carbon atoms or a substituted or unsubstituted aromatic hydrocarbon group having 6 to 12 carbon atoms; k6 and k7 are each independently an integer of 0 to 5, wherein in a case where $R^{c1}$, $R^{c2}$, $R^R$ and $R^S$ are each present in a plurality of number, a plurality of $R^{c1}$s, a plurality of $R^{c2}$s, a plurality of $R^R$s and a plurality of $R^S$s may be each identical or different with each other.

Examples of the unsubstituted linear alkyl group which may be represented by $R^{a1}$ to $R^{a3}$, $R^{b1}$, $R^{b2}$, $R^{c1}$ and $R^{c2}$ include a methyl group, an ethyl group, a n-propyl group, a n-butyl group, and the like.

Examples of the unsubstituted branched alkyl group which may be represented by $R^{a1}$ to $R^{a3}$, $R^{b1}$, $R^{b2}$, $R^{c1}$ and $R^{c2}$ include an i-propyl group, an i-butyl group, a sec-butyl group, a t-butyl group, and the like.

Examples of the unsubstituted aromatic hydrocarbon group which may be represented by $R^{a1}$ to $R^{a3}$, $R^{c1}$ and $R^{c2}$ include: aryl groups such as a phenyl group, a tolyl group, a xylyl group, a mesityl group and a naphthyl group; aralkyl groups such as a benzyl group and a phenethyl group; and the like.

Examples of the unsubstituted aromatic hydrocarbon group which may be represented by $R^{b1}$ and $R^{b2}$ include a phenyl group, a tolyl group, a benzyl group, and the like.

Examples of the divalent organic group which may be represented by $R^{b3}$ include similar groups to those exemplified as the divalent organic group which may be represented by $L^2$ in the above formula (3), and the like.

Examples of the substituent which may substitute for the hydrogen atom included in the alkyl group and the aromatic hydrocarbon group include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, the halogen atoms are preferred, and a fluorine atom is more preferred.

$R^{a1}$ to $R^{a3}$, $R^{b1}$, $R^{b2}$, $R^{c1}$ and $R^{c2}$ represent preferably an unsubstituted linear or branched alkyl group, a fluorinated alkyl group, an unsubstituted monovalent aromatic hydrocarbon group, $-OSO_2-R''$ or $-SO_2-R''$, more preferably a fluorinated alkyl group or an unsubstituted monovalent aromatic hydrocarbon group, and still more preferably a fluorinated alkyl group. R'' represents an unsubstituted monovalent alicyclic hydrocarbon group or an unsubstituted monovalent aromatic hydrocarbon group.

In the formula (G-1), k1, k2 and k3 are preferably an integer of 0 to 2, more preferably 0 and 1, and still more preferably 0. In the formula (G-2), k4 is preferably an integer of 0 to 2, more preferably 0 and 1, and still more preferably 1; k5 is preferably an integer of 0 to 2, more preferably 0 and 1, and still more preferably 0; r is preferably 2 and 3, and more preferably 2; t is preferably 0 and 1, and more preferably 0. In the formula (G-3), k6 and k7 are preferably an integer of 0 to 2, more preferably 0 and 1, and still more preferably 0.

Of these, G$^+$ represents preferably the cation (G-1), and more preferably a triphenylsulfonium cation.

Examples of the acid generating agent represented by the above formula (4) include compounds represented by the following formulae (4-1) to (4-14) (hereinafter, may be also referred to as "compounds (4-1) to (4-14)"), and the like.

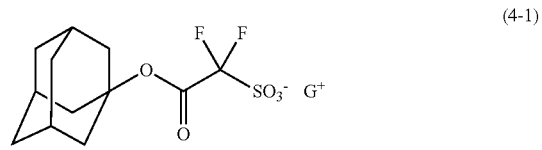

(4-1)

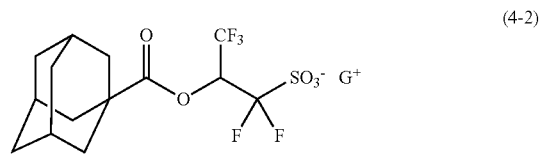

(4-2)

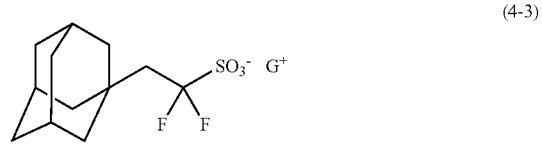

(4-3)

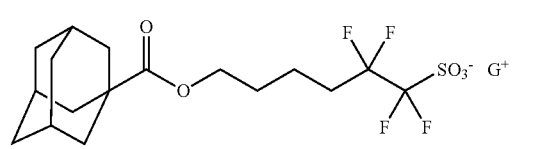

(4-4)

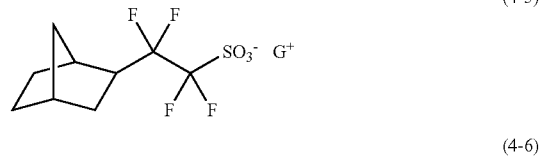

(4-5)

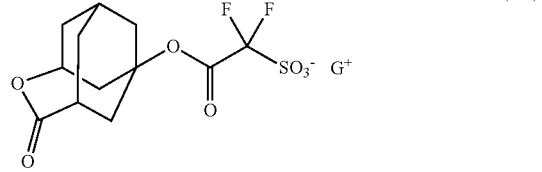

(4-6)

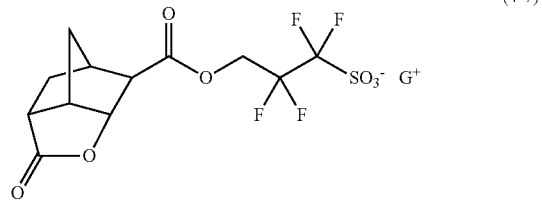

(4-7)

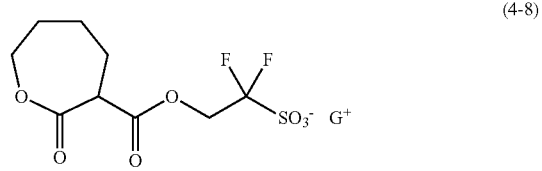

(4-8)

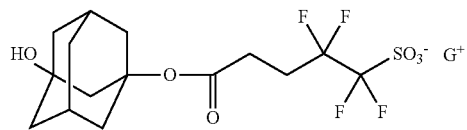
(4-9)

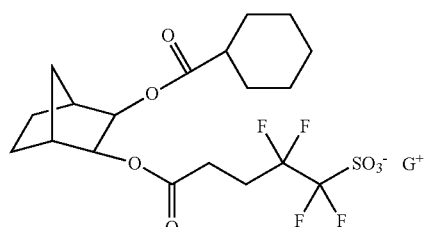
(4-10)

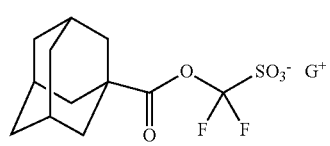
(4-11)

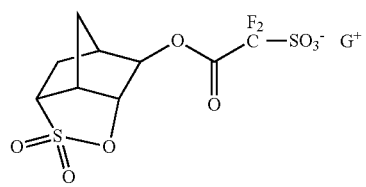
(4-12)

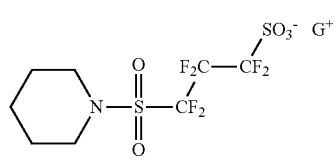
(4-13)

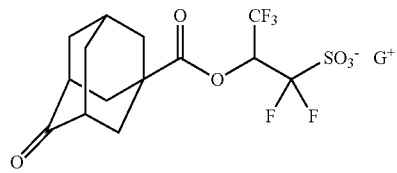
(4-14)

In the above formulae (4-1) to (4-14), G⁺ is as defined in the above formula (4).

The acid generating agent (C) is preferably an onium salt compound, more preferably a sulfonium salt, still more preferably a triphenylsulfonium salt, and particularly preferably triphenylsulfonium nonafluoro-n-butanesulfonate and the compound (4-14).

Also, the acid generator (C) is preferably a polymer in which a structure of an acid generator is incorporated as a part of the polymer such as a polymer having a structural unit represented by the following formula (5).

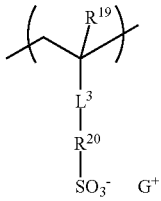
(5)

In the above formula (5), $R^{19}$ represents a hydrogen atom or a methyl group; $L^3$ represents a single bond, —COO—, —Ar—, —COO—Ar— or —Ar—OSO$_2$—; Ar represents a substituted or unsubstituted arenediyl group having 6 to 20 carbon atoms; $R^{20}$ represents a fluorinated alkanediyl group having 1 to 10 carbon atoms; and G⁺ represents a monovalent radiation-sensitive onium cation.

In a case where the acid generator (C) is the acid generating agent (C), the lower limit of the content of the acid generating agent (C) with respect to 100 parts by mass of the polymer (A) is preferably 0.1 parts by mass, more preferably 1 part by mass, still more preferably 5 parts by mass, particularly preferably 10 parts by mass, and further particularly preferably 20 parts by mass. The upper limit of the content is preferably 50 parts by mass, more preferably no greater than 40 parts by mass, still more preferably no greater than parts by mass, and particularly preferably 30 parts by mass. When the content of the acid generating agent (C) falls within the above range, a further improvement of the sensitivity of the radiation-sensitive composition is enabled. One, or two or more types of the acid generator (C) may be used.

(D) Acid Diffusion Controller

The radiation-sensitive composition may contain, as needed, the acid diffusion controller (D). The acid diffusion controller (D) exerts the effect of controlling a phenomenon of diffusion of the acid, which was generated from the compound (B) and the acid generator (C) upon the exposure, in the resist film, and inhibiting unwanted chemical reactions in an unexposed region. In addition, the storage stability of the radiation-sensitive composition is further improved, and resolution for use as a resist is more improved. Moreover, variation of the line width of the resist pattern caused by variation of post-exposure time delay from the exposure until a development treatment can be suppressed, which enables the radiation-sensitive composition with superior process stability to be obtained. The acid diffusion controller (D) may be contained in the radiation-sensitive composition either in the form incorporated as a part of the polymer or in the form of a low-molecular weight compound other than a polymer (hereinafter, may be also referred to as "(D) acid diffusion control agent" or "acid diffusion control agent (D)", as appropriate), or may be in both of these forms.

The acid diffusion control agent (D) is exemplified by a compound represented by the following formula (6a) (hereinafter, may be also referred to as "nitrogen-containing compound (I)"), a noncyclic compound having two nitrogen atoms in the same molecule (hereinafter, may be also referred to as "nitrogen-containing compound (II)"), a compound having three or more nitrogen atoms (hereinafter, may be also referred to as "nitrogen-containing compound (III)"), an amide group-containing compound, a urea compound, a nitrogen-containing heterocyclic compound, and the like.

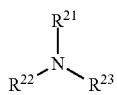
(6a)

In the above formula (6a), $R^{21}$, $R^{22}$ and $R^{23}$ each independently represent a hydrogen atom, an unsubstituted or substituted linear, branched or cyclic alkyl group, an unsubstituted or substituted aryl group or an unsubstituted or substituted aralkyl group.

Examples of the nitrogen-containing compound (I) include: monoalkylamines such as n-hexylamine; dialkylamines such as di-n-butylamine; trialkylamines such as triethylamine and tri n-pentylamine; aromatic amines such as aniline; and the like.

Examples of the nitrogen-containing compound (II) include ethylenediamine, N,N,N',N'-tetramethylethylenediamine, and the like.

Examples of the nitrogen-containing compound (III) include: polyamine compounds such as polyethylene imine and polyallylamine; polymers of dimethylaminoethylacrylamide, etc., and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include: pyridines such as pyridine and 2-methylpyridine; morpholines such as N-propylmorpholine and N-(undecan-1-ylcarbonyloxyethyl)morpholine; imidazoles such as imidazole, 2-phenylimidazole and 2,4,5-triphenylimidazole; pyrazine, pyrazole, and the like.

Also, as the nitrogen-containing organic compound, a compound having an acid-labile group may be used. Examples of the nitrogen-containing heterocyclic compound having an acid-labile group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-t-butoxycarbonyl-4-hydroxypiperidine, N-t-amyloxycarbonyl-4-hydroxypiperidine, and the like.

In addition, a photodegradable base which is sensitized upon an exposure to generate a weak acid can be also used as the acid diffusion control agent (D). The photodegradable base is exemplified by an onium salt compound and the like that loses acid diffusion controllability through degradation upon an exposure. Examples of the onium salt compound include a sulfonium salt compound represented by the following formula (6b-1), and an iodonium salt compound represented by the following formula (6b-2), and the like.

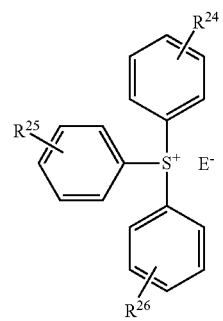
(6b-1)

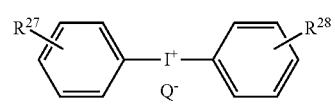
(6b-2)

In the above formulae (6b-1) and (6b-2), $R^{24}$ to $R^{28}$ each independently represent a hydrogen atom, an alkyl group, an alkoxy group, a hydroxy group or a halogen atom; $E^-$ and $Q^-$ each independently represent $OH^-$, $R^\beta$—$COO^-$, $R^\beta$—$SO_3^-$ or an anion represented by the following formula (6b-3), wherein $R^\beta$ represents an alkyl group, an aryl group or aralkyl group.

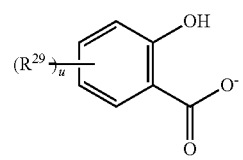
(6b-3)

In the above formula (6b-3), $R^{29}$ represents a linear or branched alkyl group having 1 to 12 carbon atoms, or a linear or branched alkoxyl group having 1 to 12 carbon atoms, wherein a part or all of hydrogen atoms included in the linear or branched alkyl group or the linear or branched alkoxy group may be substituted with a fluorine atom; and u is an integer of 0 to 2, wherein in a case where u is 2, two $R^{29}$s may be identical or different.

Examples of the photodegradable base include compounds shown below.

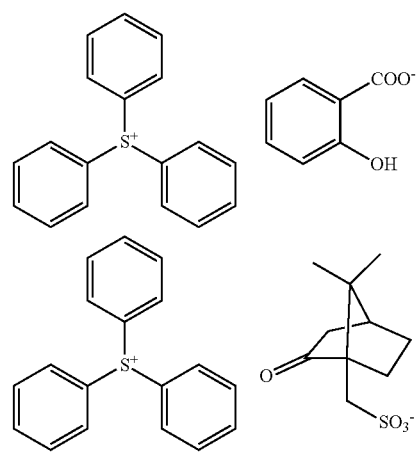

-continued

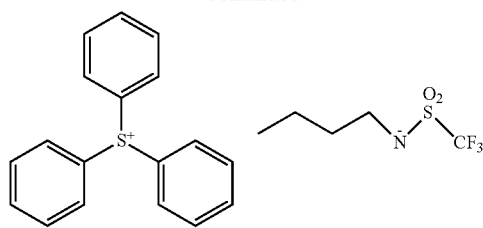

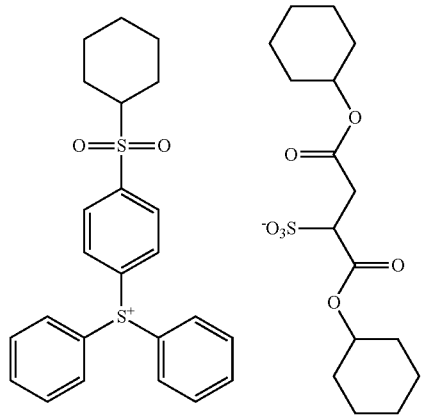

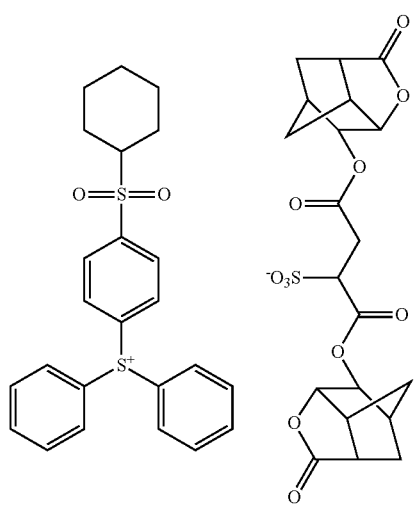

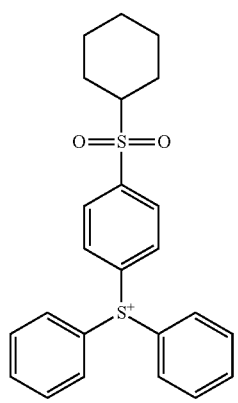

-continued

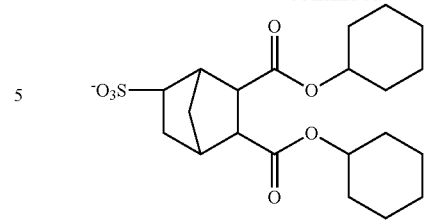

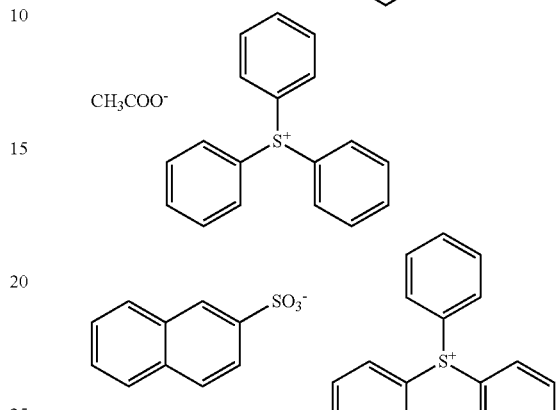

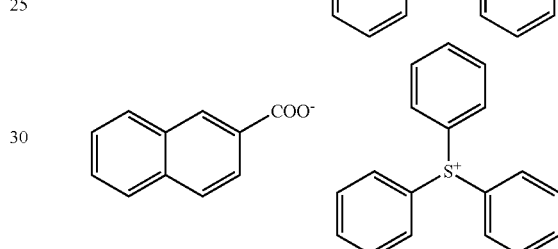

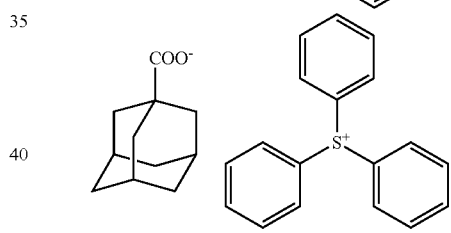

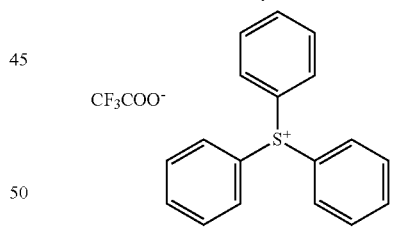

Of these, the photodegradable base is preferably a sulfonium salt, more preferably a triaryl sulfonium salt, and still more preferably triphenylsulfonium salicylate and triphenylsulfonium 10-camphorsulfonate.

Furthermore, the acid diffusion control agent (D) is acceptable as long as it is photosensitive upon an exposure to generate an acid that is weaker than the acid generated from the compound (B), and an organic acid metal salt such as zinc (II) acetate or silver (I) cyclohexanebutyrate, or the like may be also used.

In a case where the radiation-sensitive composition contains the acid diffusion controller (D), when the acid diffusion controller (D) is the acid diffusion control agent (D), the lower limit of the content of the acid diffusion controller (D)

with respect to 100 parts by mass of the polymer (A) is preferably 0.1 parts by mass, more preferably 0.5 parts by mass, still more preferably 1 part by mass, and particularly preferably 1.5 parts by mass. The upper limit of the content is preferably 20 parts by mass, more preferably 15 parts by mass, still more preferably 10 parts by mass, and particularly preferably 5 parts by mass. When the content of the acid diffusion controller (D) falls within the above range, more improvements of the resolution, storage stability, etc., of the radiation-sensitive composition are enabled.

(E) Polymer

The polymer (E) has a total percentage content by mass of fluorine atoms and silicon atoms being greater than the polymer (A). When the radiation-sensitive composition contains the polymer (E), in forming the resist film, the polymer (E) tends to be localized in the surface region of the resist film due to oil-repellent characteristics of the fluorine atom-containing polymer in the resist film. The localization of the polymer (E) in the surface region of the resist film leads to further inhibition of defects of the pattern to be formed. In addition, the polymer (E) localized in the surface region of the resist film enables the acid generator, the acid diffusion controller and the like used in liquid immersion lithography, etc., to be prevented from elution into the liquid immersion medium. Moreover, due to the water-repellent characteristics of the polymer (E), an advancing contact angle of a liquid immersion medium on the resist film can be controlled to fall within a desired range, thereby enabling generation of bubble defects to be more inhibited. Furthermore, a greater receding contact angle of the liquid immersion medium on the resist film is attained, whereby an exposure by high-speed scanning without being accompanied by residual water beads is enabled. Thus, when the radiation-sensitive composition further contains the polymer (E), forming a resist film suitable for liquid immersion lithography is enabled.

The lower limit of the total percentage content by mass of fluorine atoms and silicon atoms of the polymer (E) is preferably 1% by mass, more preferably 2% by mass, still more preferably 4% by mass, and particularly preferably 7% by mass. The upper limit of the total percentage content by mass is preferably 60% by mass, more preferably 50% by mass, still more preferably 40% by mass, and particularly preferably 30% by mass. When the total percentage content by mass of fluorine atoms and silicon atoms when falls within the above range, a more appropriate adjustment of the localization of the polymer (E) in the resist film is enabled. It is to be noted that the total percentage content by mass of fluorine atoms and silicon atoms of the polymer may be obtained by determining the structure of the polymer with a $^{13}$C-NMR spectrometry, and calculation from the structure.

The mode of incorporation of the fluorine atom and silicon atom in the polymer (E) is not particularly limited, and the fluorine atom and the silicon atom may bond to any of the main chain, a side chain and an end of the polymer (E); however, in a case where the fluorine atom is incorporated in the polymer (E), it is preferred that the polymer (E) has a structural unit that includes a fluorine atom (hereinafter, may be also referred to as "structural unit (F)"). In addition to the structural unit (F), the polymer (E) preferably has a structural unit that includes an acid-labile group in light of a more improvement of a development defects-inhibiting property of the radiation-sensitive composition. Exemplary structural unit that includes an acid-labile group includes the structural unit (I) in the polymer (A), and the like.

Furthermore, the polymer (E) preferably has an alkali-labile group. Due to the polymer (E) having the alkali-labile group, the surface of the resist film can be effectively changed from hydrophobic to hydrophilic in a development with an alkali, whereby a defects-inhibiting property of the radiation-sensitive composition is more improved. The "alkali-labile group" as referred to means a group that substitutes for a hydrogen atom of a carboxy group, a hydroxy group or the like, and that dissociates in an alkali aqueous s solution (for example, a 2.38% by mass aqueous tetramethylammonium hydroxide solution at 23° C.).

The structural unit (F) is preferably a structural unit represented by the following formula (f-1) (hereinafter, may be also referred to as "structural unit (F-1)") and a structural unit represented by the following formula (f-2) (hereinafter, may be also referred to as "structural unit (F-2)"). The structural unit (F) may have one, or two or more types of each of the structural unit (F-1) and the structural unit (F-2).

Structural Unit (F-1)

The structural unit (F-1) is represented by the following formula (f-1). Due to having the structural unit (F-1), the polymer (E) enables an adjustment of the percentage content by mass of fluorine atoms.

(f-1)

In the above formula (f-1), $R^a$ represents a hydrogen atom, a fluorine atom, a methyl group or a trifluoromethyl group; G represents a single bond, an oxygen atom, a sulfur atom, —COO—, —SO$_2$ONH—, —CONH— or —OCONH—; $R^b$ represents a monovalent fluorinated chain hydrocarbon group having 1 to 6 carbon atoms or a monovalent fluorinated alicyclic hydrocarbon group having 4 to 20 carbon atoms.

$R^a$ represents preferably a hydrogen atom or a methyl group in light of a degree of copolymerization of the monomer that gives the structural unit (F-1), and more preferably a methyl group.

G represents preferably —COO—, —SO$_2$ONH—, —CONH— or —OCONH—, and more preferably —COO—.

Examples of the monovalent fluorinated chain hydrocarbon group having 1 to 6 carbon atoms which may be represented by $R^b$ include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro-n-propyl group, a perfluoro-i-propyl group, a perfluoro-n-butyl group, a perfluoro-i-butyl group, a perfluoro-t-butyl group, a 2,2,3,3,4,4,5,5-octafluoropentyl group, a perfluorohexyl group, and the like.

Examples of the monovalent fluorinated alicyclic hydrocarbon group having 4 to 20 carbon atoms which may be represented by $R^b$ include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

$R^b$ represents preferably the fluorinated chain hydrocarbon group, more preferably a 2,2,2-trifluoroethyl group or a 1,1,1,3,3,3-hexafluoro-2-propyl group, and still more preferably a 2,2,2-trifluoroethyl group.

In a case where the polymer (E) has the structural unit (F-1), the lower limit of the proportion of the structural unit (F-1) contained with respect to the total structural units constituting the polymer (E) is preferably 10 mol %, and more preferably 20 mol %. The upper limit of the proportion is preferably 90 mol %, more preferably 70 mol %, and more preferably 50 mol %. When the proportion of the structural unit (F-1) falls within the above range, a further appropriate adjustment of the percentage content by mass of fluorine atoms of the polymer (E) is enabled.

Structural Unit (F-2)

The structural unit (F-2) is represented by the following formula (f-2). Due to having the structural unit (F-2), the polymer (E) enables an adjustment of the percentage content by mass of fluorine atoms, and also can be hydrophilic to an alkaline developer solution and/or enables the surface of the resist film to be changed from being water repellent to hydrophilic after the development with an alkali.

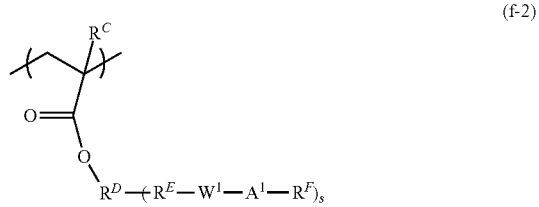

(f-2)

In the above formula (f-2), $R^C$ represents a hydrogen atom, a fluorine atom, a methyl group or a trifluoromethyl group; $R^D$ represents a hydrocarbon group having 1 to 20 carbon atoms and having a valency of (s+1), or a structure in which an oxygen atom, a sulfur atom, —NR'—, a carbonyl group, —COO— or —CONH— bonds to an end of the hydrocarbon group on a side of $R^E$; R' represents a hydrogen atom or a monovalent hydrocarbon group having 1 to 10 carbon atoms; $R^E$ represents a single bond or a divalent organic group having 1 to 20 carbon atoms; $W^1$ represents a single bond or a divalent fluorinated chain hydrocarbon group having 1 to 20 carbon atoms; $A^1$ represents an oxygen atom, —NR"—, —COO—* or —SO$_2$O—*; R" represents a hydrogen atom or a monovalent hydrocarbon group having 1 to 10 carbon atoms, wherein * denotes a site of bonding to $R^F$; $R^F$ represents a hydrogen atom or a monovalent organic group having 1 to 30 carbon atoms; and s is an integer of 1 to 3, wherein, in a case where s is 1, $R^D$ may be a single bond, in a case where s is 2 or 3, a plurality of $R^E$s may be identical or different, W's may be identical or different, A's may be identical or different and $R^F$s may be identical or different, and in a case where $W^1$ represents a single bond, $R^F$ represents a group that includes a fluorine atom.

$R^C$ represents preferably a hydrogen atom or a methyl group in light of e.g., a degree of copolymerization of the monomer that gives the structural unit (F-2), and more preferably a methyl group.

Exemplary hydrocarbon group having 1 to 20 carbon atoms and having a valency of (s+1) which may be represented by $R^D$ includes a group obtained by removing s hydrogen atoms from the monovalent hydrocarbon group having 1 to 20 carbon atoms exemplified as $R^7$ to $R^9$ in the above formula (2-2), and the like.

In the above formula, s is preferably 1 and 2, and more preferably 1.

$R^D$ represents, in a case where s is 1, preferably a single bond or a divalent hydrocarbon group, more preferably a single bond or an alkanediyl group, still more preferably a single bond or an alkanediyl group having 1 to 4 carbon atoms, and particularly preferably a single bond, a methanediyl group or a propanediyl group.

Exemplary divalent organic group having 1 to 20 carbon atoms which may be represented by $R^E$ includes a group obtained by removing one hydrogen atom from the monovalent organic group having 1 to 20 carbon atoms exemplified as $R^{p1}$ in the above formula (A), and the like.

$R^E$ represents preferably a single bond or a group having a lactone structure, more preferably a single bond or a group having a polycyclic lactone structure, and still more preferably a single bond or a group having a norbornanelactone structure.

Examples of the divalent fluorinated chain hydrocarbon group having 1 to 20 carbon atoms which may be represented by $W^1$ include:

fluorinated alkanediyl groups such as a fluoromethanediyl group, a difluoromethanediyl group, a fluoroethanediyl group, a difluoroethanediyl group, a tetrafluoroethanediyl group, a hexafluoropropanediyl group and an octafluorobutanediyl group;

fluorinated alkenediyl groups such as a fluoroethenediyl group and a difluoroethenediyl group; and the like. Of these, the fluorinated alkanediyl group is preferred, and a difluoromethanediyl group is more preferred.

$A^1$ represents preferably an oxygen atom, —COO—* or —SO$_2$—*, and more preferably —COO—*.

The monovalent organic group having 1 to 30 carbon atoms which may be represented by $R^F$ is exemplified by an alkali-labile group, an acid-labile group, a hydrocarbon group having 1 to 30 carbon atoms, and the like. Of these, $R^F$ represents preferably an alkali-labile group. Due to $R^F$ representing the alkali-labile group, the surface of the resist film can be more effectively changed from hydrophobic to hydrophilic in a development with an alkali, whereby the development defects-inhibiting property of the radiation-sensitive composition is further improved.

In a case where $R^F$ represents the alkali-labile group, $R^F$ is preferably groups represented by the following formulae (iii) to (v) (hereinafter, may be also referred to as "groups (iii) to (v)").

(iii)

In the above formula (iii), $R^{5a}$ and $R^{5b}$ each independently represent a monovalent organic group having 1 to 20 carbon atoms, or $R^{5a}$ and $R^{5b}$ taken together represent an alicyclic structure having 3 to 20 ring atoms together with the carbon atom to which $R^{5a}$ and $R^{5b}$ bond.

(iv)

In the above formula (iv), $R^{5c}$ and $R^{5d}$ each independently represent a monovalent organic group having 1 to 20 carbon atoms, or $R^{5c}$ and $R^{5d}$ taken together represent a hetero ring structure having 3 to 20 ring atoms together with the nitrogen atom to which $R^{5a}$ and $R^{5d}$ bond.

$$—R^{5e} \tag{v}$$

In the above formula (v), $R^{5e}$ represents a monovalent hydrocarbon group having 1 to 20 carbon atoms or a monovalent fluorinated hydrocarbon group having 1 to 20 carbon atoms.

The monovalent organic group having 1 to 20 carbon atoms and the monovalent hydrocarbon group having 1 to 20 carbon atoms are exemplified by a similar group to the group exemplified as $R^{p1}$ in the above formula (A), and the like.

Exemplary monovalent fluorinated hydrocarbon group having 1 to 20 carbon atoms includes a group obtained from the group exemplified as the monovalent hydrocarbon group having 1 to 20 carbon atoms by substituting a part or all of hydrogen atoms included therein with a fluorine atom, and the like.

The group (iii) is preferably groups represented by the following formulae (iii-1) to (iii-4) (hereinafter, may be also referred to as "groups (iii-1) to (iii-4)"); the group (iv) is preferably a group represented by the following formula (iv-1) (hereinafter, may be also referred to as "group (iv-1)"); and the group (v) is preferably groups represented by the following formulae (v-1) to (v-5) (hereinafter, may be also referred to as "groups (v-1) to (v-5)").

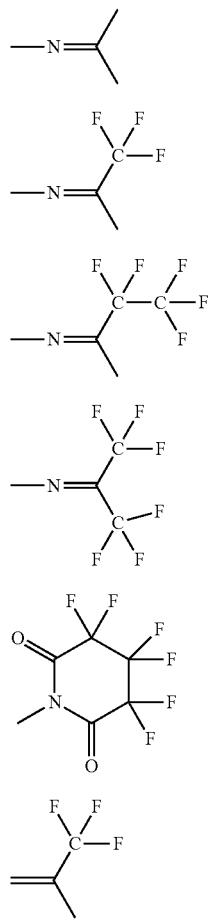

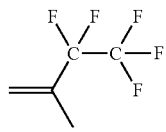

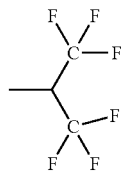

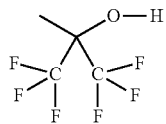

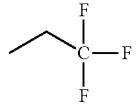

Of these, the group (v-3) and the group (v-5) are preferred.

In addition, $R^F$ representing a hydrogen atom is preferred since affinity of the polymer (E) to an alkaline developer solution is improved. In this instance, the affinity is further improved when $A^1$ represents an oxygen atom and $W^1$ represents a 1,1,1,3,3,3-hexafluoro-2,2-propanediyl group.

In a case where the polymer (E) has the structural unit (F-2), the lower limit of the proportion of the structural unit (F-2) contained with respect to the total structural units constituting the polymer (E) is preferably 10 mol %, more preferably 20 mol %, and more preferably 40 mol %. The upper limit of the proportion is preferably 90 mol %, more preferably 85 mol %, and more preferably 80 mol %. When the proportion of the structural unit (F-2) falls within the above range, more appropriate change of the surface of the resist film formed from the radiation-sensitive composition, from being water repellent to hydrophilic after the development with an alkali is enabled.

The lower limit of the proportion of the structural unit (F) contained with respect to the total structural units constituting the polymer (E) is preferably 10 mol %, more preferably 20 mol %, and more preferably 25 mol %. The upper limit of the proportion is preferably 90 mol %, more preferably 85 mol %, and more preferably 80 mol %.

The lower limit of the proportion of the structural unit that includes the acid-labile group contained in the polymer (E) with respect to the total structural units constituting the polymer (E) is preferably 10 mol %, more preferably 20 mol %, and more preferably 50 mol %. The upper limit of the proportion is preferably 90 mol %, more preferably 80 mol %, and more preferably 75 mol %. When the proportion of the structural unit that includes the acid-labile group falls within the above range, a further improvement of the defects-inhibiting property of the radiation-sensitive composition is enabled.

In a case where the radiation-sensitive composition contains the polymer (E), the lower limit of the content of the polymer (E) with respect to 100 parts by mass of the polymer (A) is preferably 0.1 parts by mass, more preferably 0.5 parts by mass, still more preferably 1 part by mass, and particularly preferably 2 parts by mass. The upper limit of the content is preferably 20 parts by mass, more preferably 15 parts by mass, still more preferably 10 parts by mass, and particularly preferably 5 parts by mass. The radiation-sensitive composition may contain one, or two or more types of the polymer (E).

The polymer (E) may be synthesized by a similar method to the polymer (A) described above.

The lower limit of the Mw of the polymer (E) as determined by GPC is preferably 1,000, more preferably 3,000, still more preferably 4,000, and particularly preferably 5,000. The upper limit of the Mw is preferably 50,000, more preferably 30,000, still more preferably 20,000, and particularly preferably 10,000. When the Mw of the polymer (E) falls within the above range, a coating property and the defects-inhibiting property of the radiation-sensitive composition are more improved.

The lower limit of a ratio (Mw/Mn) of the Mw to Mn the of polymer (E) as determined by GPC is typically 1, and preferably 1.2. The upper limit of the ratio is preferably 5, more preferably 3, and still more preferably 2.

(F) Solvent

The radiation-sensitive composition typically contains (F) a solvent. The solvent (F) is not particularly limited as long as it is capable of dissolving or dispersing at least the polymer (A), the compound (B), as well as the acid generator (C) and the acid diffusion controller (D), etc., contained as desired.

The solvent (F) is exemplified by an alcohol solvent, an ether solvent, a ketone solvent, an amide solvent, an ester solvent, a hydrocarbon solvent, and the like.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether, and the like.

Examples of the ether solvent include:

dialkyl ether solvents such as diethyl ether, dipropyl ether and dibutyl ether;

cyclic ether solvents such as tetrahydrofuran and tetrahydropyran;

aromatic ring-containing ether solvents such as diphenyl ether and anisole (methyl phenyl ether); and the like.

Examples of the ketone solvent include:

chain ketone solvents such as acetone, methyl ethyl ketone, methyl-n-propyl ketone, methyl n-butyl ketone, diethyl ketone, methyl iso-butyl ketone, 2-heptanone (methyl n-pentylketone), ethyl n-butyl ketone, methyl-n-hexyl ketone, di-iso-butyl ketone and trimethylnonanone:

cyclic ketone solvents such as cyclopentanone, cyclohexanone, cycloheptanone, cyclooctanone and methylcyclohexanone:

2,4-pentanedione, acetonylacetone, acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

acetic acid ester solvents such as methyl acetate, ethyl acetate, n-propyl acetate, iso-propyl acetate, n-butyl acetate, iso-butyl acetate, sec-butyl acetate, n-pentyl acetate, i-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

lactone solvents such as γ-butyrolactone and δ-valerolactone;

carbonate solvents such as dimethyl carbonate, diethyl carbonate, ethylene carbonate and propylene carbonate;

lactic acid ester solvents such as methyl lactate, ethyl lactate, n-butyl lactate and n-amyl lactate;

glycol diacetate, methoxytriglycol acetate, ethyl propionate, n-butyl propionate, iso-amyl propionate, diethyl oxalate, di-n-butyl oxalate, methyl acetoacetate, ethyl acetoacetate, diethyl malonate, dimethyl phthalate, diethyl phthalate, and the like.

Examples of the hydrocarbon solvent include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Of these, the ester solvents and the ketone solvents are preferred, the polyhydric alcohol partial ether acetate solvent, the ester lactate solvent and the cyclic ketone solvent are more preferred, and propylene glycol monomethyl ether acetate, ethyl lactate and cyclohexanone are still more preferred. The radiation-sensitive composition may contain one, or two or more types of the solvent (F).

Other Optional Component

The radiation-sensitive composition may contain as other optional component such as, for example, a surfactant, in addition to the components (A) to (F) described above. The radiation-sensitive composition may contain one, or two or more types of each of the other optional components.

Surfactant

The surfactant exerts the effect of improving the coating property, striation, developability, and the like. Examples of the surfactant include: nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; and the like, as well as commercially available products such as: KP341 (Shin-Etsu Chemical Co., Ltd.), Polyflow No. 75 and Polyflow No. 95 (all available from Kyoeisha Chemical Co., Ltd.), EFTOP EF301, EFTOP EF303 and EFTOP EF352 (all available from Tochem Products Co. Ltd.), Megaface F171 and Megaface F173 (all available from DIC, Corporation), Fluorad FC430 and Fluorad FC431 (all available from Sumitomo 3M Limited), ASAHI GUARD AG710, Surflon S-382, Surflon SC-101, Surflon SC-102, Surflon SC-103, Surflon SC-104, Surflon SC-105 and Surflon SC-106 (all available from Asahi Glass Co., Ltd.); and the like. The upper limit of the content of the surfactant with respect to 100 parts by mass of the polymer (A) is preferably 2 parts by mass.

Preparation Method of Radiation-Sensitive Composition

The radiation-sensitive composition may be prepared by mixing, for example, the polymer (A), the compound (B), as well as the optional component which may be added as needed, and the solvent (F) in a certain ratio, and preferably filtering a thus resulting mixture through a membrane filter having a pore size of about 0.2 μm. The lower limit of the solid content concentration of the radiation-sensitive composition is preferably 0.1% by mass, more preferably 0.5% by mass, still more preferably 1% by mass, and particularly preferably 1.5% by mass. The upper limit of the solid content concentration is preferably 50% by mass, more preferably 30% by mass, still more preferably 10% by mass, and particularly preferably 5% by mass.

The radiation-sensitive composition may be used for any of positive tone pattern formation in which an alkaline developer solution is employed, and negative tone pattern formation in which a developer solution containing an organic solvent is employed.

Pattern-Forming Method

The pattern-forming method includes the steps of: forming a film (hereinafter, may be also referred to as "film-forming step"); exposing the film (hereinafter, may be also referred to as "exposure step"); and developing the film exposed (hereinafter, may be also referred to as "development step"). In the pattern-forming method, the film is formed from the radiation-sensitive composition described above. According to the pattern-forming method, formation of a pattern accompanied by small nanoedge roughness is enabled with high sensitivity since the aforementioned radiation-sensitive composition is used. Each step will be described below.

Film-Forming Step

In this step, the radiation-sensitive composition is used to form the film. The film formation may be carried out by, for example, applying a radiation-sensitive composition onto a substrate. Although an application procedure is not particularly limited, application means such as e.g., spin-coating, cast coating or roll coating may be employed. The substrate is exemplified by a silicon wafer, a wafer coated with aluminum, and the like. Specifically, after the radiation-sensitive composition is applied such that the resultant film has a predetermined thickness, prebaking (PB) is executed as needed to evaporate off the solvent in the coating film.

The lower limit of the average thickness of the film is preferably 1 nm, more preferably 10 nm, still more preferably 20 nm, and particularly preferably 30 nm. The upper limit of the average thickness is preferably 1,000 nm, more preferably 200 nm, still more preferably 100 nm, and particularly preferably 70 rm.

The lower limit of the temperature of PB is typically 60° C., and preferably 80° C. The upper limit of the temperature of PB is typically 140° C., and preferably 120° C. The lower limit of the time period of PB is typically 5 sec, and preferably 10 sec. The upper limit of the time period of PB is typically 600 sec, and preferably 300 sec.

Exposure Step

In this step, the film formed in the film-forming step is exposed. The exposure is carried out by irradiating with a radioactive ray through a mask having a predetermined pattern via a liquid immersion medium such as water, as the case may be. Examples of the radioactive ray include: electromagnetic waves such as a visible light ray, an ultraviolet ray, a far ultraviolet ray, a vacuum ultraviolet ray (extreme ultraviolet ray (EUV); wavelength: 13.5 nm), an X-ray and a γ-ray; charged particle rays such as an electron beam and an α-ray; and the like. Of these, radioactive rays that allow more secondary electrons to be released from the compound (B) by the exposure are preferred, and EUV and an electron beam are more preferred.

In addition, post exposure baking (PEB) may be carried out after the exposure. The lower limit of the temperature of PEB is typically 50° C., and preferably 80° C. The upper limit of the temperature of PEB is typically 180° C., and preferably 130° C. The lower limit of the time period of PEB is typically 5 sec, and preferably 10 sec. The upper limit of the time period of PEB is typically 600 sec, and preferably 300 sec.

In the embodiment of the present invention, in order to maximize the potential ability of the radiation-sensitive composition, for example, an organic or inorganic antireflective film may be formed on the substrate employed. In addition, in order to prevent influences of basic impurities etc., included in the environment atmosphere, a protective film may be also provided on the coating film, for example. Furthermore, in a case where an exposure by way of liquid immersion is carried out, in order to avoid direct contact of the film with the liquid immersion medium, a protective film for liquid immersion may be also provided on the film, for example.

Development Step

In this step, the film exposed in the exposure step is developed. A developer solution for use in the development is exemplified by an alkali aqueous solution, an organic solvent-containing liquid, and the like.

Examples of the alkali aqueous solution include alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene and 1,5-diazabicyclo-[4.3.0]-5-nonene, and the like.

The lower limit of the content of the alkaline compound in the alkali aqueous solution is preferably 0.1% by mass, more preferably 0.5% by mass, and still more preferably 1% by mass. The upper limit of the content is preferably 20% by mass, more preferably 10% by mass, and still more preferably 5% by mass.

The alkali aqueous solution is preferably an aqueous TMAH solution, and more preferably a 2.38% by mass aqueous TMAH solution.

Exemplary organic solvent in the organic solvent-containing liquid includes those similar to the organic solvents exemplified as the solvent (F) of the radiation-sensitive composition, and the like. Of these, the ester solvents are preferred, and butyl acetate is more preferred.

The lower limit of the content of the organic solvent in the organic solvent developer solution is preferably 80% by mass, more preferably 90% by mass, still more preferably 95% by mass, and particularly preferably 99% by mass.

These developer solutions may be used either alone, or two or more types thereof in combination. It is to be noted that the development is typically followed by washing with water, etc., and drying.

A positive tone pattern can be obtained when the alkali aqueous solution is used as the developer solution. Whereas a negative tone pattern can be obtained when the organic solvent is used as the developer solution.

Radiation-Sensitive Acid Generating Agent

The radiation-sensitive acid generating agent according to another embodiment of the present invention contains a compound that includes a metal cation, an anion that is a conjugate base of an acid being sulfonic acid, nitric acid, organic azinic acid, disulfonylimidic acid or a combination thereof, the radiation-sensitive acid generating agent being capable of generating an acid by an action of EUV or an electron beam, and the acid having a pKa of no greater than 0. The radiation-sensitive acid generating agent may be suitably used as an acid generating component of the radiation-sensitive composition described above, and enables the sensitivity and nanoedge roughness performance of the radiation-sensitive composition containing the same to be improved.

The compound is preferably represented by the above formula (1).

The radiation-sensitive acid generating agent has been already described in the section "(B) Compound" of above "Radiation-Sensitive Composition".

EXAMPLES

Hereinafter, the present invention will be explained in detail by way of Examples, but the present invention is not in any way limited to these Examples. Measuring methods for physical property values in the Examples are shown below.

Weight Average Molecular Weight (Mw) and Number Average Molecular Weight (Mn)

The Mw and Mn of the polymer were measured by gel permeation chromatography (GPC) with GPC columns (G2000HXL×2; G3000HXL×1; and G4000HXL×1, all available from Tosoh Corporation), under analytical conditions involving a flow rate of 1.0 mL/min, an elution solvent of tetrahydrofuran, a sample concentration of 1.0% by mass, an amount of injected sample of 100 μL and a column temperature of 40° C., by using a differential refractometer as a detector, with mono-dispersed polystyrene as a standard.

$^{13}$C-NMR Analysis

A $^{13}$C-NMR analysis for determining the proportion of the structural unit of the polymer was performed by using a nuclear magnetic resonance apparatus (JEOL, Ltd., "JNM-ECX400"), and CDCl$_3$ as a measurement solvent, with an internal standard of tetramethylsilane (TMS).

Synthesis of Polymer

Synthesis of Polymer (A)

Monomers (M-1) to (M-6), and (M-8) used for the syntheses of the polymer (A) are shown below. The compound (M-3) gives a structural unit derived from p-hydroxystyrene. The compound (M-5) allows a structure of an acid generator to be incorporated into the polymer (A). In addition, introduction of a structural unit derived from the compound (M-7) into the polymer was carried out by: deprotecting the structural unit derived from the compound (M-3) after the synthesis of the structural unit to convert into a structural unit derived from p-hydroxystyrene; and thereafter subjecting the same to acetalization using methyl 2-methyl-1-propenyl ether in accordance with a common procedure.

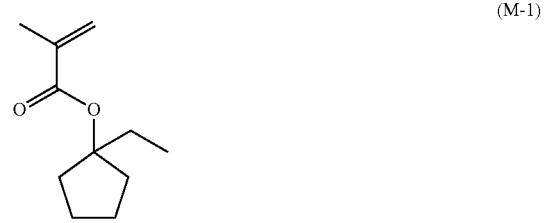

(M-1)

(M-2)

(M-3)

(M-4)

-continued

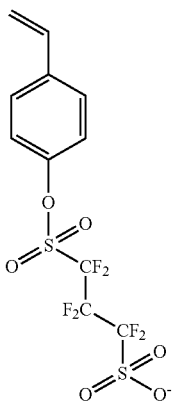
(M-5)

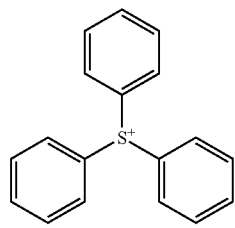
(M-6)

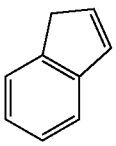
(M-7)

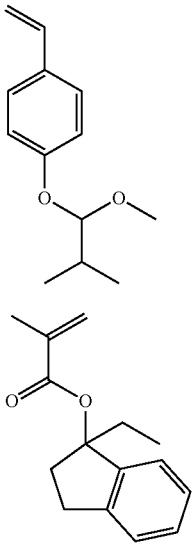
(M-8)

Synthesis Example 1

After dissolving 55 g (50 mol %) of the compound (M-2), 45 g (50 mol %) of the compound (M-1) and 3 g of AIBN in 300 g of methyl ethyl ketone, the mixture was maintained in a nitrogen atmosphere, at a reaction temperature of 78° C. to allow for polymerization for 6 hrs. After the polymerization, the reaction solution was added into 2,000 g of methanol dropwise to solidify the polymer. Next, the polymer washed with 300 g of methanol twice, and thus resultant white powder was filtered off and dried overnight under a reduced pressure at 50° C. to give a polymer (A-1). The polymer (A-1) had Mw of 7,000, and Mw/Mn of 2.10. In addition, as a result of the $^{13}$C-NMR analysis, the proportions of the structural units derived from (M-1) and (M-2) were 52 mol % and 48 mol %, respectively.

Synthesis Example 2

After dissolving 55 g (58 mol %) of the compound (M-3), 45 g (42 mol %) of the compound (M-1), 3 g of AIBN and 1 g of t-dodecyl mercaptan in 150 g of propylene glycol monomethyl ether, the mixture was maintained in a nitrogen atmosphere, at a reaction temperature of 70° C. to allow for polymerization for 16 hrs. After the polymerization, the reaction solution was added into 1,000 g of n-hexane dropwise to purify the polymer by solidification. Next, after adding 150 g of propylene glycol monomethyl ether to the polymer again, 150 g of methanol, 37 g of triethylamine and 7 g of water were further added thereto, and then a hydrolysis reaction was allowed for 8 hrs while the mixture was refluxed at a boiling point to allow for deacetylation of a structural unit derived from (M-3). After the reaction, the solvent and triethylamine was distilled off under reduced pressure, and a thus resultant polymer was dissolved in 150 g of acetone. The mixture was then added into 2,000 g of water dropwise to permit solidification, and thus resultant white powder was filtered off and dried overnight under a reduced pressure at 50° C. to give a polymer (A-2). The polymer (A-2) had Mw of 6,000, and Mw/Mn of 1.90. In addition, as a result of the $^{13}$C-NMR analysis, the proportions of the structural unit derived from p-hydroxystyrene and the structural unit derived from the compound (M-1) were 50 mol % and 50 mol %, respectively.

Synthesis Examples 3 to 5

Polymers (A-3) to (A-5) were synthesized in a similar manner to Synthesis Example 2 except that monomers of the type and in the amount shown in Table 1 below were used. Table 1 shows Mw and Mw/Mn of each polymer obtained, along with the proportion (mol %) of each structural unit as determined by the $^{13}$C-NMR analysis. The proportion of each structural unit derived from (M-3) and (M-7) in the polymer (A-4) is a value determined by the $^{13}$C-NMR measurement on the polymer (A-4) obtained by acetalization of a part of the structural unit derived from p-hydroxystyrene formed from (M-3) to give a structural unit derived from (M-7). M-3 in Table 1 corresponds to the structural unit derived from p-hydroxystyrene in the polymer.

TABLE 1

| | (A) polymer | Monomer type | proportion of structural unit contained (mol %) | Mw | Mw/Mn |
|---|---|---|---|---|---|
| Synthesis Example 1 | A-1 | M-1 | 52 | 7,000 | 2.10 |
| | | M-2 | 48 | | |
| Synthesis Example 2 | A-2 | M-1 | 50 | 6,000 | 1.90 |
| | | M-3 | 50 | | |
| Synthesis Example 3 | A-3 | M-3 | 50 | 8,500 | 1.50 |
| | | M-4 | 43 | | |
| | | M-5 | 7 | | |
| Synthesis Example 4 | A-4 | M-3 | 74 | 8,900 | 1.63 |
| | | M-6 | 10 | | |
| | | M-7 | 16 | | |
| Synthesis Example 5 | A-5 | M-3 | 66 | 9,100 | 1.72 |
| | | M-6 | 10 | | |
| | | M-8 | 24 | | |

Synthesis Example 6

A mixture obtained by dissolving 10 g of glutaraldehyde (50% by mass aqueous solution), 24.8 g of 3-methoxyphenol and 37.5 g of trifluoroacetic acid in 50 mL of chloroform was refluxed for 48 hrs. This solution was added to methanol, and thus resulting precipitate was dried in vacuo to give 11.3 g of a methoxy group-protected compound represented by the following formula (M-9). Next, 8.0 g of this compound, 8.2 g of potassium carbonate and 0.064 g of tetrabutylammonium bromide were dissolved in 95 mL of N-methylpyrrolidone (NMP), and the mixture was stirred at 60° C. for 3 hrs. Next, a mixed solution of 4.3 g of 2-bromoacetyloxy-2-methyladamantane and 5 mL of NMP was added, and the mixture was further stirred at 60° C. for 48 hrs. Next, the reaction liquid was poured into chloroform and washed with a 0.1 M aqueous oxalic acid solution, followed by drying over magnesium sulfate and filtration through Celite, and the filtrate was concentrated in vacuo. Solid deposition was allowed by adding to methanol the solution after the concentration, followed by drying under reduced pressure to give 5.9 g of the compound (A-6) protected with a 2-acetyloxy-2-methyladamantane group at 18% hydroxyl groups in the following formula (M-9).

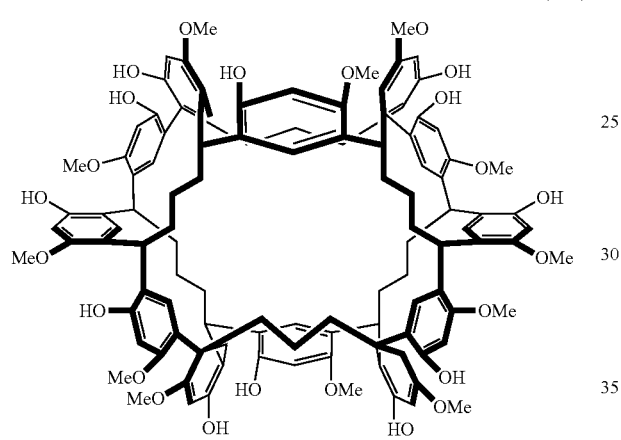
(M-9)

Synthesis of Polymer (E)

Monomers used in the syntheses of polymer (E) are shown below.

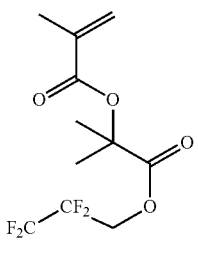
(M-10)

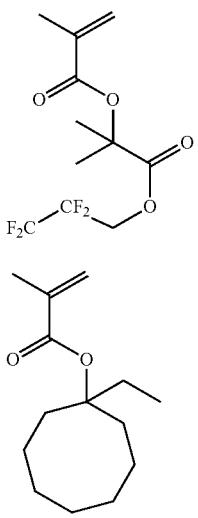
(M-11)

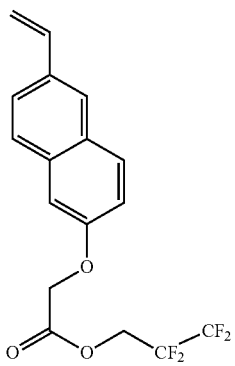
(M-12)

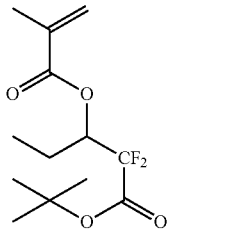
(M-13)

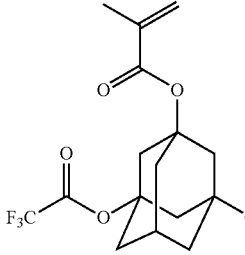
(M-14)

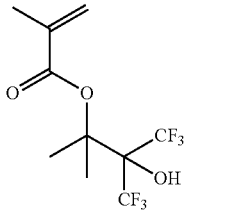
(M-15)

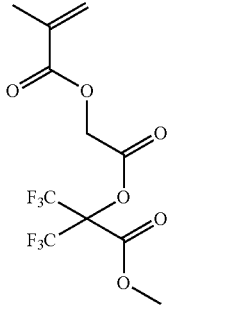
(M-16)

Synthesis Example 7

Into a three-neck flask equipped with a thermometer and a reflux condenser, 12.4 g (41 mmol) of the compound (M-10), 3.0 g (13.5 mmol) of the compound (M-11) and 23 g of tetrahydrofuran (THF) were added to permit dissolution. To the solution thus obtained was added 11 mmol of dimethyl azobisisobutyrate as a polymerization initiator and dissolved. The solution was added dropwise over 3 hrs in a nitrogen atmosphere to 12.87 g of tetrahydrofuran heated to 67° C., thereby allowing for a polymerization reaction. After completion of the dropwise addition, the reaction liquid was stirred for 4 hrs with heating, Thereafter, the reaction liquid was cooled to room temperature. The polymerization reaction liquid thus obtained was added to a large amount of n-heptane dropwise to precipitate the polymer. The precipitated polymer by this operation was filtered off, washed and dried to give 3 g of a polymer (E-1). The polymer (E-1) had Mw of 21,500, and Mw/Mn of 1.25. In addition, as a result of the $^{13}$C-NMR analysis, the proportions of the structural units derived from (M-10) and (M-11) were 78 mol % and 22 mol %, respectively.

Synthesis Examples 8 and 9

Polymers (E-2) and (E-3) were obtained by allowing the polymerization reaction similarly to Synthesis Example 7, by using the monomers of the type and in the amount and the solvents for polymerization shown in Table 2 below at the polymerization temperature and for the polymerization time period shown in Table 2, and thereafter precipitating the polymer with the polymer precipitation solvent shown in Table 2. It is to be noted that in the synthesis of (E-2), the polymerization reaction liquid was concentrated in vacuo and then mixed with the polymer precipitation solvent. Meanwhile, in the synthesis of the polymer (E-3), the polymerization reaction liquid was concentrated in vacuo and adjusted to give a 40% by mass solution of the polymer in toluene/methyl ethyl ketone (mass ratio: 9/1), and then mixed with the polymer precipitation solvent. Table 2 shows Mw and Mw/Mn of each polymer obtained, along with the proportion (mol %) of each structural unit.

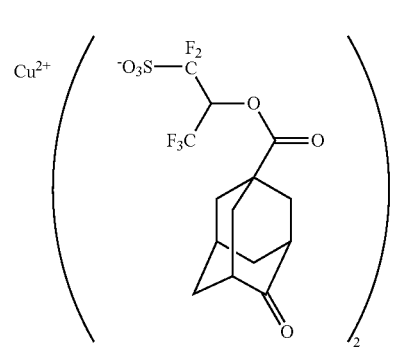

B-3: zinc (II) trifluoromethanesulfonate

B-4: a compound represented by the following formula (B-4)

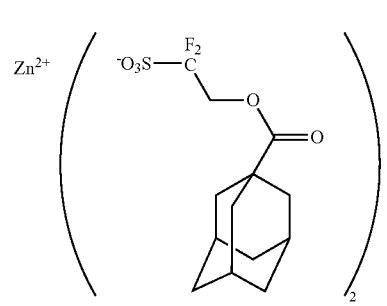

TABLE 2

| (E) Polymer | | Solvent for polymerization | Polymerization temperature | Polymerization time period | Polymer precipitation solvent | Monomer type | Proportion of structural unit contained (mol %) | Mw | Mw/Mn |
|---|---|---|---|---|---|---|---|---|---|
| Synthesis Example 7 | E-1 | THF | 67° C. | 4 hrs | heptane | M-10<br>M-11 | 78<br>22 | 21,500 | 1.25 |
| Synthesis Example 8 | E-2 | THF | 80° C. | 6 hrs | heptane | M-12<br>M-13 | 59<br>41 | 11,700 | 1.44 |
| Synthesis Example 9 | E-3 | methyl ethyl ketone | 80° C. | 2 hrs | hexane | M-14<br>M-15<br>M-16 | 32<br>35<br>33 | 8,800 | 1.45 |

Preparation of Radiation-Sensitive Composition

Each component used for the preparation of the radiation-sensitive compositions, other than the polymer (A) and the polymer (E), are shown below.

(B) Compound

Regarding each compound (B) in the following, pKa of the acid (I) generated from the compound (B) by irradiation with a radioactive ray, and the value of van der Waals volume of the generated acid (I) are shown in Table 3 below.

B-1: copper (II) trifluoromethanesulfonate

B-2: a compound represented by the following formula (B-2)

B-5: barium (II) nonafluorobutanesulfonate

B-6: a compound represented by the following formula (B-6)

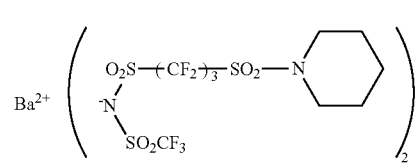

B-7: lanthanum (III) nitrate

B-8: a compound represented by the following formula (B-8)

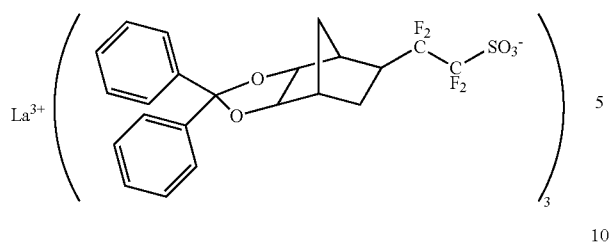

B-9: cerium (III) trifluoromethanesulfonate
B-10: cerium (III) 2-dodecylbenzenesulfonate
B-11: yttrium (III) trifluoromethanesulfonate
B-12: a compound represented by the following formula (B-12)

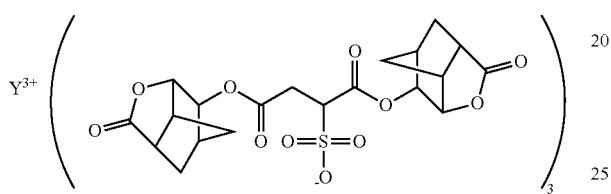

B-13: indium (III) trifluoromethanesulfonate
B-14: a compound represented by the following formula (B-14)

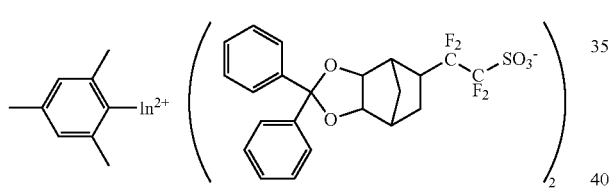

B-15: tetrabutylammonium trifluoromethanesulfonate

TABLE 3

| (B) Compound | pKa of generated acid (I) | van der Waals volume of generated acid (I) (×10⁻²⁸ m³) |
|---|---|---|
| B-1 | −3.4 | 0.84 |
| B-2 | −2.1 | 3.0 |
| B-3 | −3.4 | 0.84 |
| B-4 | −1.6 | 2.6 |
| B-5 | −3.3 | 1.7 |
| B-6 | −0.4 | 2.7 |
| B-7 | −1.4 | 0.42 |
| B-8 | −2.1 | 3.7 |
| B-9 | −3.4 | 0.84 |
| B-10 | −1.6 | 3.3 |
| B-11 | −3.4 | 0.84 |
| B-12 | −0.7 | 3.8 |
| B-13 | −3.4 | 0.84 |
| B-14 | −2.1 | 3.7 |
| B-15 | −3.4 | 0.84 |

(C) Acid Generating Agent

C-1: triphenylsulfonium nonafluoro-n-butanesulfonate (a compound represented by the following formula (C-1))

C-2: triphenylsulfonium 2-(4-oxo-adamantan-1-ylcarbonyloxy)-1,1,3,3,3-pentafluoropropane-1-sulfonate (a compound represented by the following formula (C-2))

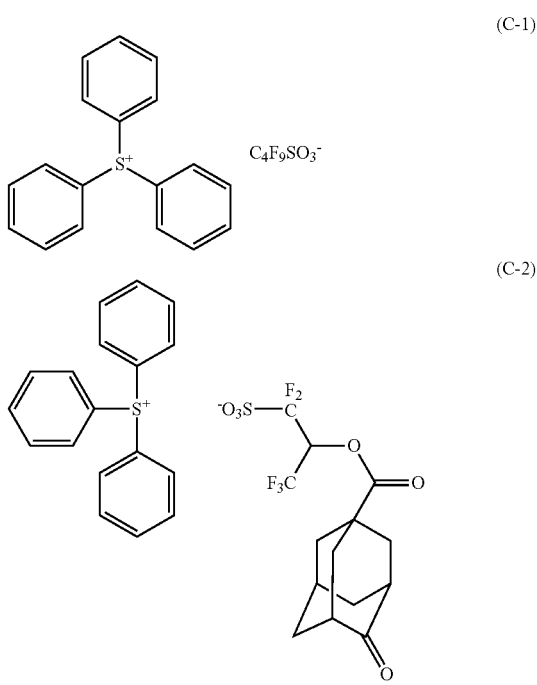

(D) Acid Diffusion Control Agent

D-1: triphenylsulfonium salicylate (a compound represented by the following formula (D-1))

D-2: 2,4,5-triphenylimidazole (a compound represented by the following formula (D-2))

D-3: zinc (II) acetate (pKa of acetic acid: 4.76)

D-4: silver (I) cyclohexanebutyrate (pKa of cyclohexanebutyric acid: 4.95)

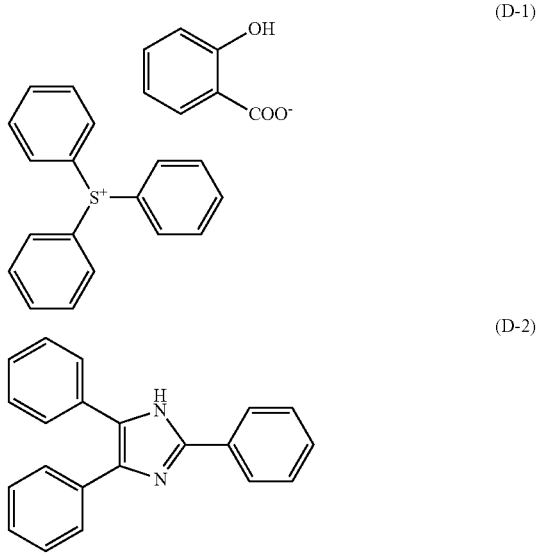

(F) Solvent

F-1: propylene glycol monomethyl ether acetate
F-2: ethyl lactate
F-3: cyclohexanone

Example 1

After mixing 100 parts by mass of (A-1) as the polymer (A), 3 parts by mass of (B-1) as the compound (B), 27 parts by mass of (C-1) as the acid generating agent (C), 2.6 parts of by mass of (D-1) as the acid diffusion control agent (D), and as the solvent (F), 4,300 parts by mass of (F-1) and 1,900 parts by mass of (F-3), thus resulting mixed liquid was filtered through a membrane filter having a pore size of 0.20 µm to prepare a radiation-sensitive composition (R-2).

Reference Example 1 to 6, Examples 2 to 21 and Comparative Examples 1 to 3

Radiation-sensitive compositions (R-1) and (R-3) to (R-30) were prepared in a similar manner to Example 1 except that each component of the type and the content shown in Table 4 below was used. The denotation "-" in columns of the components in Table 4 indicates that a corresponding component was not used.

It is noted that the compound (D-3) in Comparative Example 2 includes a metal cation, and the acid generated from the anion (I) has a pKa of greater than 0 (pKa of acetic acid: 4.76).

Pattern Formation

Example 1

After the radiation-sensitive composition (R-2) prepared in Example 1 was spin-coated on a silicon wafer in "CLEAN TRACK ACT-8" available from Tokyo Electron Limited, PB was carried out under a condition at 110° C. for 60 sec to form a resist film having an average thickness of 50 nm. Subsequently, patterning was executed by irradiating with an electron beam using a simplified electron beam writer ("HL800D" available from Hitachi, Ltd., power: 50 KeV, electric current density: 5.0 ampere/cm$^2$). After the irradiation with the electron beam, PEB was carried out in the CLEAN TRACK ACT-8 under a condition at 100° C. for 60 sec. Thereafter, a 2.38% by mass aqueous tetramethylammonium hydroxide (TMAH) solution was used to carry out a development in accordance with a puddle procedure in the CLEAN TRACK ACT-8 at 23° C. for 1 min. Subsequently, washing with pure water and drying resulted in formation of a positive tone resist pattern.

Reference Examples 1 to 6, Examples 2 to 21 and Comparative Examples 1 to 3

Each positive tone resist pattern was formed in a similar manner to Example 1 except that the radiation-sensitive composition shown in Table 4 below was used.

Evaluations

Evaluations of sensitivity and nanoedge roughness performance were made on the positive tone resist pattern formed as described above in accordance with the following method. The results of the evaluations are shown together in Table 4. It is to be noted that the denotation "-" in columns of the EB evaluation column indicates a standard for the evaluation.

Sensitivity

In patterning with the electron beam writer (EB), an exposure dose at which a line-and-space pattern (1L 1S) configured with a line part having a line width of 150 nm and a space part formed by neighboring line parts with an interval of 150 nm was formed to give a line width of 1:1 was defined as "optimal exposure dose", and the sensitivity (µC/cm$^2$) was defined based on the optimal exposure dose. As compared with corresponding Reference Example, evaluations were made as: "A (favorable)" in the case of the improvement of the sensitivity being estimated to be no less than 30%; and "B (unfavorable)" in the case of the improvement of the sensitivity being estimated to be less than 30%. It is to be noted that the corresponding Reference Example was: Reference Example 1 for Examples 1 and 2; Reference Example 2 for Examples 3 to 7, 18, 19 and Comparative Examples 1 to 3; Reference Example 3 for Examples 8 and 9; Reference Example 4 for Examples 10 to 12; Reference Example 5 for Examples 13 to 15, 20, 21; and Reference Example 6 for Examples 16 and 17.

Nanoedge Roughness Performance

Figure 2:
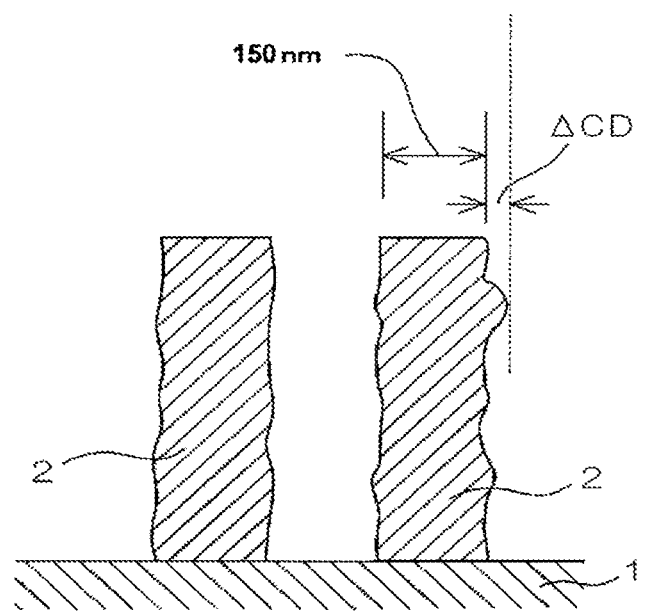
FIG. 2 shows a schematic cross sectional view illustrating a line-pattern configuration.

In the patterning with the electron beam writer, the line patterns of the line-and-space pattern (1L 1S) were observed by using a high-resolution FEB critical dimension measurement device ("S-9220", available from Hitachi, Ltd.). Arbitrary twenty points on the substrate were observed, and with respect to the configuration at each observation point, a difference "ΔCD" between an intended line width of 150 nm and a line width in an area in which irregularities generated along the side lateral surface 2a of the line part 2 of the resist film formed on the silicon wafer 1 was most significant was measured as shown in FIGS. 1 and 2. The nanoedge roughness performance (nm) was defined based on the average value of the ΔCD values. As compared with the nanoedge roughness of Reference Example, evaluations were made as: "AA (very favorable)" in the case of the value being decreased or equivalent, or increased by less than 15%; "A (favorable)" in the case of the value being no less than 15% and less than 30%; and "B (unfavorable)" in the case of the value being no less than 30%.

TABLE 4

| | Radiation-sensitive composition | (A) Polymer type | (A) Polymer amount blended (parts by mass) | (B) Compound type | (B) Compound amount blended (parts by mass) | (C) Acid generating agent type | (C) Acid generating agent amount blended (parts by mass) | (D) Acid diffusion control agent type | (D) Acid diffusion control agent amount blended (parts by mass) |
|---|---|---|---|---|---|---|---|---|---|
| Reference Example 1 | R-1 | A-1 | 100 | — | — | C-1 | 27 | D-1 | 2.6 |
| Example 1 | R-2 | A-1 | 100 | B-1 | 3 | C-1 | 27 | D-1 | 2.6 |
| Example 2 | R-3 | A-1 | 100 | B-2 | 3 | C-1 | 27 | D-1 | 2.6 |
| Reference Example 2 | R-4 | A-2 | 100 | — | — | C-1 | 20 | D-1 | 2.6 |

TABLE 4-continued

| | | | | | | | | | (E) Polymer | | (F) Solvent | | EB evaluation | |
|---|---|---|---|---|---|---|---|---|---|---|---|---|---|---|
| | | | | | | | | | type | amount blended (parts by mass) | type | amount blended (parts by mass) | Sensitivity | Nanoedge roughness |
| Reference Example 1 | | | | | | | | | — | — | F-1/F-3 | 4,300/1,900 | — | — |
| Comparative Example 1 | R-5 | A-2 | 100 | — | — | C-1 | 30 | D-1 | 2.6 | | | | | |
| Example 1 | | | | | | | | | — | — | F-1/F-3 | 4,300/1,900 | A | A |
| Example 2 | | | | | | | | | — | — | F-1/F-3 | 4,300/1,900 | A | AA |
| Reference Example 2 | | | | | | | | | — | — | F-1/F-2 | 4,300/1,900 | — | — |
| Example 3 | R-6 | A-2 | 100 | B-7 | 3 | — | — | D-1 | 2.6 | | | | | |
| Comparative Example 1 | | | | | | | | | — | — | F-1/F-2 | 4,300/1,900 | B | B |
| Example 4 | R-7 | A-2 | 100 | B-7 | 1 | C-1 | 20 | D-1 | 2.6 | | | | | |
| Example 5 | R-8 | A-2 | 100 | B-8 | 3 | C-1 | 20 | D-1 | 2.6 | | | | | |
| Example 6 | R-9 | A-2 | 100 | B-7 | 1 | C-1 | 20 | D-3 | 2.0 | | | | | |
| Example 7 | R-10 | A-2 | 100 | B-7 | 1 | C-1 | 20 | D-4 | 2.0 | | | | | |
| Example 3 | | | | | | | | | — | — | F-1/F-2 | 4,300/1,900 | A | A |
| Example 4 | | | | | | | | | — | — | F-1/F-2 | 4,300/1,900 | A | A |
| Example 5 | | | | | | | | | — | — | F-1/F-2 | 4,300/1,900 | A | AA |
| Example 6 | | | | | | | | | — | — | F-1/F-2 | 4,300/1,900 | A | A |
| Example 7 | | | | | | | | | — | — | F-1/F-2 | 4,300/1,900 | A | A |
| Reference Example 3 | R-11 | A-3 | 100 | — | — | C-2 | 23 | D-1 | 2.2 | E-1 | 3 | F-1 | 5,800 | — | — |
| Example 8 | R-12 | A-3 | 100 | B-3 | 3 | C-2 | 23 | D-1 | 2.2 | E-1 | 3 | F-1 | 5,800 | A | A |
| Example 9 | R-13 | A-3 | 100 | B-4 | 3 | C-2 | 23 | D-1 | 2.2 | E-1 | 3 | F-1 | 5,800 | A | AA |
| Reference Example 4 | R-14 | A-4 | 100 | — | — | C-2 | 23 | D-2 | 2.2 | E-2 | 3 | F-1 | 5,800 | — | — |
| Example 10 | R-15 | A-4 | 100 | B-5 | 3 | — | — | D-2 | 2.2 | E-2 | 3 | F-1 | 5,800 | A | A |
| Example 11 | R-16 | A-4 | 100 | B-5 | 1 | C-2 | 23 | D-2 | 2.2 | E-2 | 3 | F-1 | 5,800 | A | A |
| Example 12 | R-17 | A-4 | 100 | B-6 | 3 | C-2 | 23 | D-2 | 2.2 | E-2 | 3 | F-1 | 5,800 | A | AA |
| Reference Example 5 | R-18 | A-5 | 100 | — | — | C-2 | 23 | D-1 | 2.2 | E-3 | 3 | F-1 | 5,800 | — | — |
| Example 13 | R-19 | A-5 | 100 | B-9 | 3 | — | — | D-1 | 2.2 | E-3 | 3 | F-1 | 5,800 | A | A |
| Example 14 | R-20 | A-5 | 100 | B-9 | 1 | C-2 | 23 | D-1 | 2.2 | E-3 | 3 | F-1 | 5,800 | A | A |
| Example 15 | R-21 | A-5 | 100 | B-10 | 3 | C-2 | 23 | D-1 | 2.2 | E-3 | 3 | F-1 | 5,800 | A | AA |
| Reference Example 6 | R-22 | A-6 | 100 | — | — | C-1 | 30 | D-2 | 2.5 | — | — | F-1 | 5,800 | — | — |
| Example 16 | R-23 | A-6 | 100 | B-3 | 3 | C-1 | 30 | D-2 | 2.5 | — | — | F-1 | 5,800 | A | A |
| Example 17 | R-24 | A-6 | 100 | B-4 | 3 | C-1 | 30 | D-2 | 2.5 | — | — | F-1 | 5,800 | A | A |
| Example 18 | R-25 | A-2 | 100 | B-13 | 1 | C-1 | 20 | D-1 | 2.6 | — | — | F-1/F-2 | 4,300/1,900 | A | A |
| Example 19 | R-26 | A-2 | 100 | B-14 | 3 | C-1 | 20 | D-1 | 2.6 | — | — | F-1/F-2 | 4,300/1,900 | A | AA |
| Example 20 | R-27 | A-5 | 100 | B-11 | 1 | C-2 | 23 | D-1 | 2.2 | E-3 | 3 | F-1 | 5,800 | A | A |
| Example 21 | R-28 | A-5 | 100 | B-12 | 3 | C-2 | 23 | D-1 | 2.2 | E-3 | 3 | F-1 | 5,800 | A | AA |
| Comparative Example 2 | R-29 | A-2 | 100 | — | — | C-1 | 20 | D-3 | 2.0 | | | | | | |
| Comparative Example 3 | R-30 | A-2 | 100 | B-15 | 3 | C-1 | 20 | D-1 | 2.6 | | | | | | |

TABLE 4-continued

| | | | | | | |
|---|---|---|---|---|---|---|
| Comparative Example 2 | — | — | F-1/F-2 | 4,300/1,900 | B | A |
| Comparative Example 3 | — | — | F-1/F-2 | 4,300/1,900 | B | AA |

As is seen from the results shown in Table 4, the radiation-sensitive compositions of Examples were superior in the sensitivity and the nanoedge roughness performance. It is to be noted that since similar tendencies have been known to exist between the cases of the EUV exposure and the exposure to electron beams, superior sensitivity and nanoedge roughness performance may be expected for the radiation-sensitive compositions of Examples even in the case of the EUV exposure.

According to the radiation-sensitive composition and the pattern-forming method of the embodiments of the present invention, formation of a pattern accompanied by small nanoedge roughness is enabled with high sensitivity. The radiation-sensitive acid generating agent of the embodiment of the present invention can be suitably used as an acid generating component of the radiation-sensitive composition. Therefore, these can be suitably used in manufacture of semiconductor devices in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive composition comprising:
a first polymer comprising a first structural unit which comprises an acid-labile group; and
a first compound comprising a metal cation and a first anion that is a conjugate base of an acid,
the acid having a pKa of no greater than 0,
wherein the first compound is a sulfonic acid metal salt of formula (A)

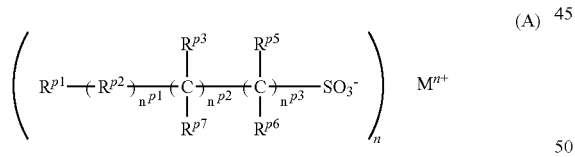

(A)

where $R^{p1}$ represents a hydrogen atom, a fluorine atom or a monovalent organic group having 1 to 20 carbon atoms;
$R^{p2}$ represents a divalent linking group;
$R^{p3}$ and $R^{p4}$ each independently represent a hydrogen atom, a fluorine atom, a monovalent hydrocarbon group having 1 to 20 carbon atoms, or a monovalent fluorinated hydrocarbon group having 1 to 20 carbon atoms;
$R^{p5}$ and $R^{p6}$ each independently represent a fluorine atom or a monovalent fluorinated hydrocarbon group having 1 to 20 carbon atoms;
$n^{p1}$ is an integer of 0 to 10;
$n^{p2}$ is an integer of 0 to 10;
$n^{p3}$ is an integer of 1 to 10,
wherein in a case where $n^{p1}$ is no less than 2, a plurality of $R^{p2}$s are identical or different,
in a case where $n^{p2}$ is no less than 2, a plurality of $R^{p3}$s are identical or different, and a plurality of $R^{p4}$s are identical or different, and
in a case where $n^{p3}$ is no less than 2, a plurality of $R^{p5}$s are identical or different, and a plurality of $R^{p6}$s are identical or different;
$M^{n+}$ represents the metal cation having a valency of n;
n is an integer of 1 to 4; and
the metal cation is a cation of copper, zinc, barium, lanthanum, cerium, yttrium, indium or silver.

2. The radiation-sensitive composition according to claim 1, wherein a van der Waals volume of the acid is no less than $2.5 \times 10^{-28}$ m$^3$.

3. The radiation-sensitive composition according to claim 1, wherein the first structural unit is a structural unit represented by formula (2-1), a structural unit represented by formula (2-2) or a combination thereof,

(2-1)

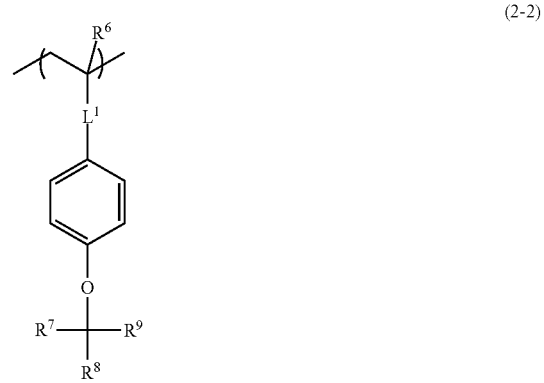

(2-2)

wherein, in the formula (2-1),
$R^2$ represents a hydrogen atom, a fluorine atom, a methyl group or a trifluoromethyl group;
$R^3$ represents a monovalent hydrocarbon group having 1 to 20 carbon atoms; and
$R^4$ and $R^5$ each independently represent a monovalent hydrocarbon group having 1 to 20 carbon atoms, or $R^4$ and $R^5$ taken together represent an alicyclic structure having 3 to 20 ring atoms together with the carbon atom to which these groups bond, and
in the formula (2-2),
$R^6$ represents a hydrogen atom or a methyl group;
$L^1$ represents a single bond, —COO— or —CONH—;
$R^7$ represents a hydrogen atom or a monovalent hydrocarbon group having 1 to 20 carbon atoms; and $R^8$ and $R^9$ each independently represent a monovalent hydrocarbon group having 1 to 20 carbon atoms, or a monovalent oxyhydrocarbon group having 1 to 20 carbon atoms.

4. The radiation-sensitive composition according to claim 1, wherein the first polymer further comprises a second structural unit represented by formula (3):

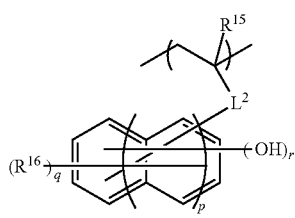

(3)

wherein, in the formula (3), $R^{15}$ represents a hydrogen atom or a methyl group;

$L^2$ represents a single bond or a divalent organic group having 1 to 20 carbon atoms;

$R^{16}$ represents a monovalent organic group having 1 to 20 carbon atoms;

p is an integer of 0 to 2;

q is an integer of 0 to 9, wherein in a case where q is no less than 2, a plurality of $R^{16}$s are identical or different; and r is an integer of 1 to 3.

5. The radiation-sensitive composition according to claim 1, wherein a content of the first compound with respect to 100 parts by mass of the first polymer is no less than 0.1 parts by mass and no greater than 200 parts by mass.

6. The radiation-sensitive composition according to claim 1, further comprising a radiation-sensitive acid generator other than the first compound.

7. The radiation-sensitive composition according to claim 1, further comprising a second polymer having a total percentage content by mass of fluorine atoms and silicon atoms greater than the first polymer.

8. A pattern-forming method comprising:

forming a film from the radiation-sensitive composition according to claim 1;

exposing the film; and developing the film exposed.

9. A radiation-sensitive acid generating agent, comprising:

a compound which comprises:
 a metal cation; and
 an anion that is a conjugate base of an acid which is sulfonic acid, wherein the radiation-sensitive acid generating agent is capable of generating the acid by an action of EUV or an electron beam, the acid has a pKa of no greater than 0, and the compound is a sulfonic acid metal salt of formula (A)

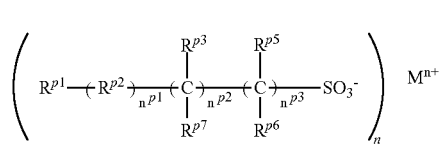

(A)

where $R^{p1}$ represents a hydrogen atom, a fluorine atom or a monovalent organic group having 1 to 20 carbon atoms;

$R^{p2}$ represents a divalent linking group;

$R^{p3}$ and $R^{p4}$ each independently represent a hydrogen atom, a fluorine atom, a monovalent hydrocarbon group having 1 to 20 carbon atoms, or a monovalent fluorinated hydrocarbon group having 1 to 20 carbon atoms;

$R^{p5}$ and $R^{p6}$ each independently represent a fluorine atom or a monovalent fluorinated hydrocarbon group having 1 to 20 carbon atoms;

$n^{p1}$ is an integer of 0 to 10;

$n^{p2}$ is an integer of 0 to 10;

$n^{p3}$ is an integer of 1 to 10, wherein in a case where no is no less than 2, a plurality of $R^{p2}$s are identical or different, in a case where $n^{p2}$ is no less than 2, a plurality of $R^{p3}$s are identical or different, and a plurality of $R^{p4}$s are identical or different, and in a case where $n^{p3}$ is no less than 2, a plurality of $R^{p5}$s are identical or different, and a plurality of $R^{p6}$s are identical or different;

$M^{n+}$ represents the metal cation having a valency of n;

n is an integer of 1 to 4; and the metal cation is a cation of copper, zinc, barium, lanthanum, cerium, yttrium, indium or silver.

10. The radiation-sensitive composition according to claim 1, wherein the sulfonic acid metal salt is one of compounds (i-1) to (i-15):

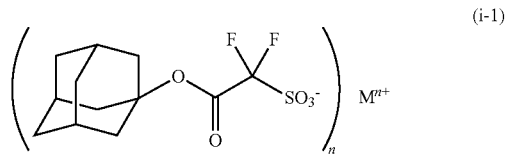

(i-1)

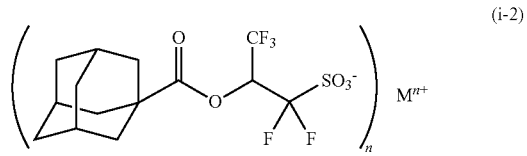

(i-2)

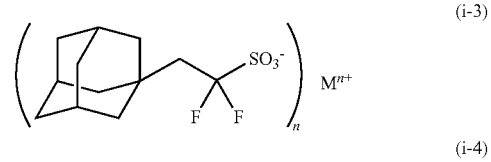

(i-3)

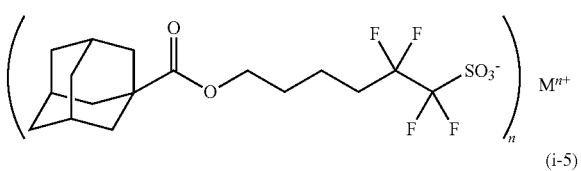

(i-4)

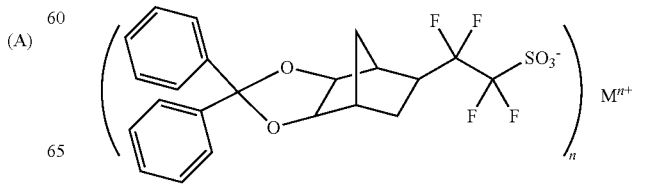

(i-5)

73
-continued

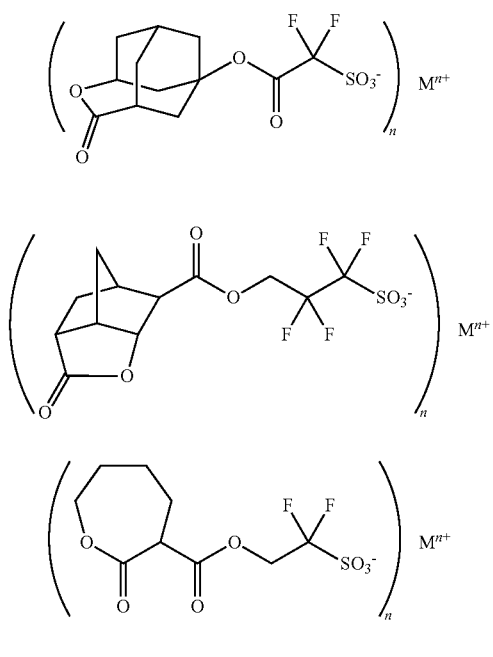

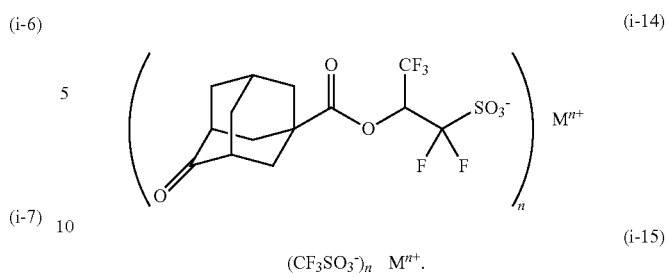

11. The radiation-sensitive composition according to claim 10, wherein the sulfonic acid metal salt is one of the compounds (i-3), (i-5), (i-14), and (i-15).

12. The radiation-sensitive composition according to claim 10, wherein the sulfonic acid metal salt is one of a zinc (II) compound of (i-3), a lanthanum (III) compound of (i-5), an indium (III) compound of (i-5), a copper (II) compound of (i-14), a copper (II) compound of (i-15), a zinc (II) compound of (i-15), and a cerium (III) compound of (i-15).

13. The radiation-sensitive composition according to claim 1, wherein the sulfonic acid metal salt is one of a compound (B-2), a compound (B-4), and a compound (B-8):

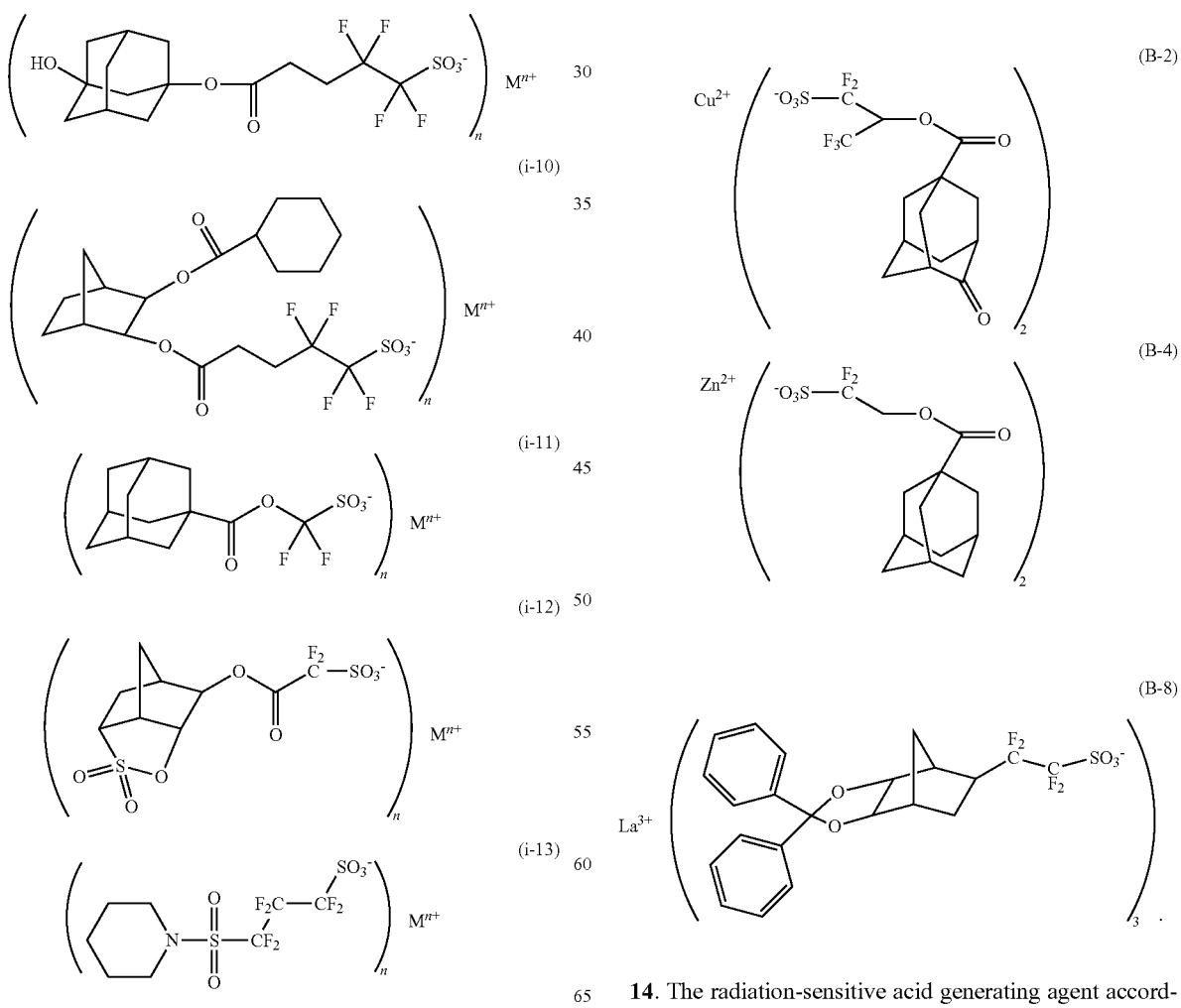

14. The radiation-sensitive acid generating agent according to claim 9, wherein the sulfonic acid metal salt is one of compounds (i-1) to (i-15):

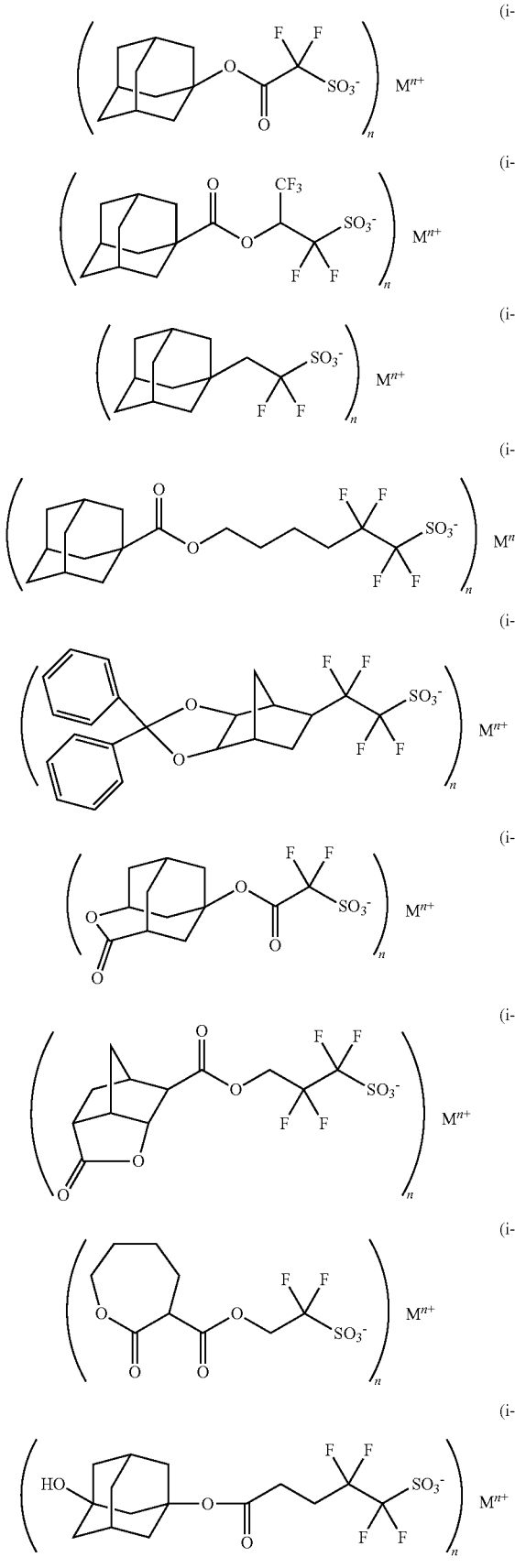
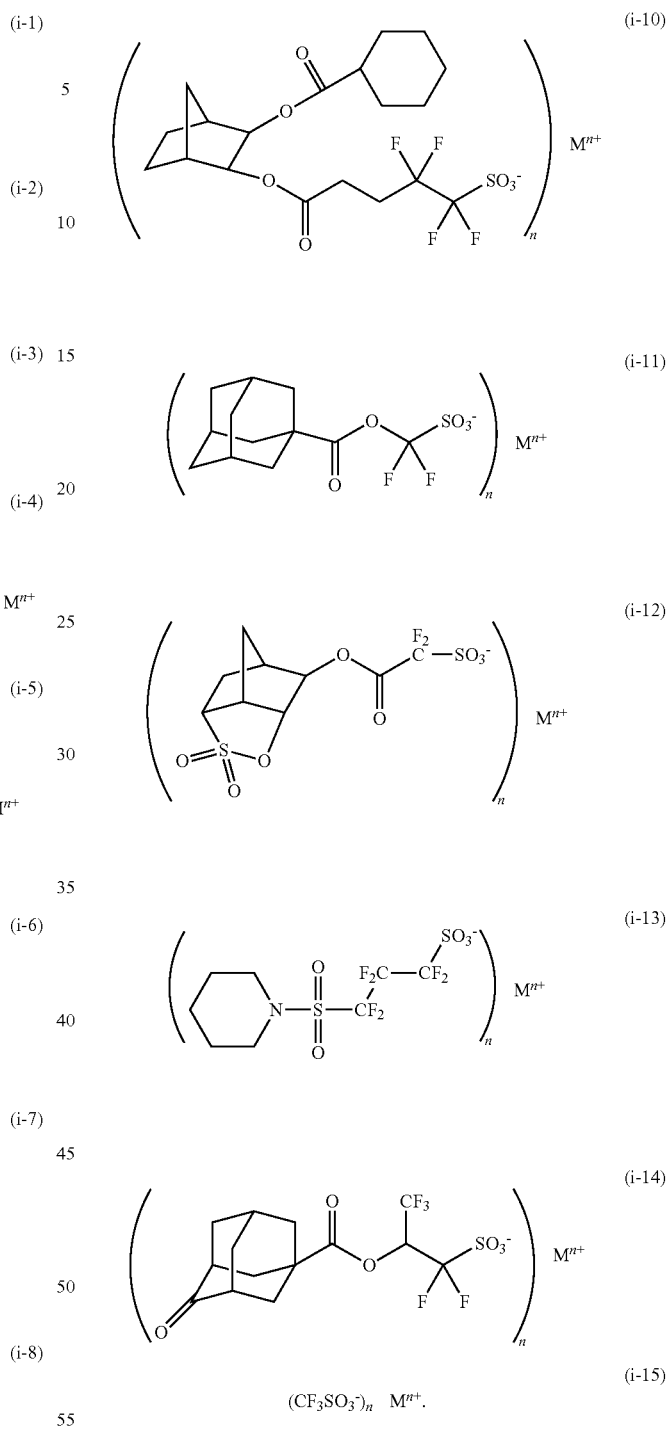

15. The radiation-sensitive acid generating agent according to claim 14, wherein the sulfonic acid metal salt is one of the compounds (i-3), (i-5), (i-14), and (i-15).

16. The radiation-sensitive acid generating agent according to claim 14, wherein the sulfonic acid metal salt is one of a zinc (II) compound of (i-3), a lanthanum (III) compound of (i-5), an indium (III) compound of (i-5), a copper (II) compound of (i-14), a copper (II) compound of (i-15), a zinc (II) compound of (i-15), and a cerium (III) compound of (i-15).

17. The radiation-sensitive acid generating agent according to claim 9, wherein the sulfonic acid metal salt is one of a compound (B-2), a compound (B-4), and a compound (B-8):
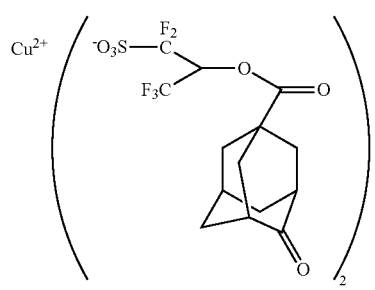
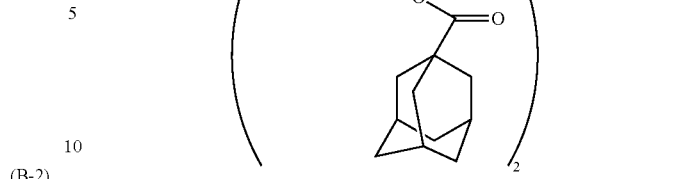
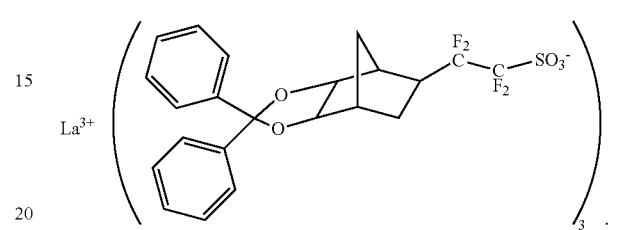
* * * * *

UNITED STATES PATENT AND TRADEMARK OFFICE
CERTIFICATE OF CORRECTION

PATENT NO.         : 11,204,552 B2
APPLICATION NO.    : 15/988436
DATED              : December 21, 2021
INVENTOR(S)        : Tomoki Nagai et al.

Page 1 of 1

It is certified that error appears in the above-identified patent and that said Letters Patent is hereby corrected as shown below:

In the Claims

At Column 69, Lines 45-50, in Claim 1, delete:

"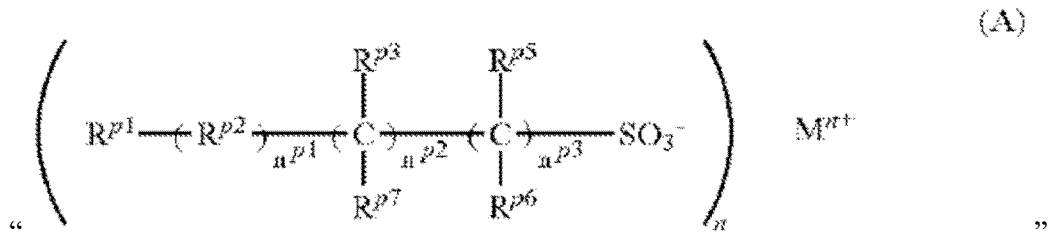"

And insert:

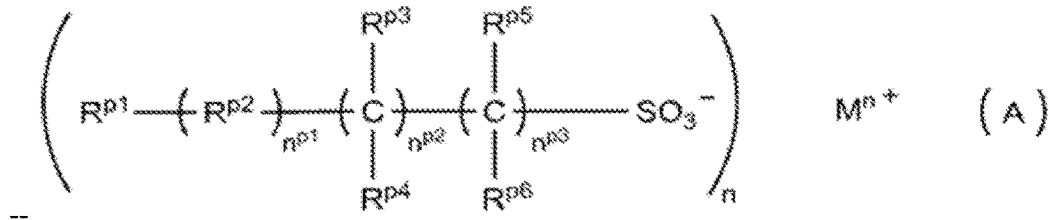

--                                                   --

Signed and Sealed this
Third Day of May, 2022

Katherine Kelly Vidal
*Director of the United States Patent and Trademark Office*